United States Patent
Muller et al.

(10) Patent No.: US 6,656,964 B2
(45) Date of Patent: Dec. 2, 2003

(54) METHOD OF INHIBITING PHOSPHODIESTERASES WITH SUBSTITUTED ALKANOHYDROXAMIC ACIDS

(75) Inventors: George W. Muller, Bridgewater, NJ (US); Hon-Wah Man, Neshanic Station, NJ (US)

(73) Assignee: Celgene Corporation, Warren, NJ (US)

( * ) Notice: Subject to any disclaimer, the term of this patent is extended or adjusted under 35 U.S.C. 154(b) by 0 days.

(21) Appl. No.: 09/780,725

(22) Filed: Feb. 9, 2001

(65) Prior Publication Data

US 2001/0049371 A1 Dec. 6, 2001

Related U.S. Application Data

(60) Division of application No. 09/126,157, filed on Jul. 30, 1998, now Pat. No. 6,214,857, which is a continuation-in-part of application No. 08/903,975, filed on Jul. 31, 1997, now abandoned.

(51) Int. Cl.$^7$ ............................................. A61K 31/405
(52) U.S. Cl. ..................... 514/417; 514/247; 514/248; 514/259; 514/272; 514/309; 514/315; 514/412; 514/418; 514/419; 514/424; 514/425
(58) Field of Search ................................. 514/247, 248, 514/259, 272, 309, 315, 412, 417, 418, 419, 424, 425

(56) References Cited

U.S. PATENT DOCUMENTS 6,214,857 B1 * 4/2001 Muller et al. ............... 514/417

* cited by examiner

Primary Examiner—Bennett Celsa
(74) Attorney, Agent, or Firm—Mathews, Collins, Shepherd & McKay, P.A.

(57) ABSTRACT

Imido and amido substituted alkanohydroxamic acids reduce the levels of TNFα and inhibit phosphodiesterase in a mammal. A typical embodiment is 3-(3-cyclopentyloxy-4-methoxyphenyl)-N-hydroxy-3-phthalimidopropionamide.

11 Claims, No Drawings

METHOD OF INHIBITING PHOSPHODIESTERASES WITH SUBSTITUTED ALKANOHYDROXAMIC ACIDS

CROSS-REFERENCE TO RELATED APPLICATIONS

This is a division of Ser. No. 09/126,157, filed Jul. 30, 1998, now U.S. Pat. No. 6,214,857, which in turn is a continuation-in-part of Ser. No. 08/903,975, filed Jul. 31, 1997, now abandoned.

FIELD OF THE INVENTION

The present invention relates to imido and amido substituted alkanohydroxamic acids, the method of reducing levels of tumor necrosis factor α in a mammal through the administration thereof, and pharmaceutical compositions of such derivatives.

BACKGROUND OF THE INVENTION

Tumor necrosis factor α, or TNFα, is a cytokine which is released primarily by mononuclear phagocytes in response to a number immunostimulators. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions. These include endotoxemia and/or toxic shock syndrome {Tracey et al., *Nature* 330, 662–664 (1987) and Hinshaw et al., *Circ. Shock* 30, 279–292 (1990)}; cachexia {Dezube et al., *Lancet*, 335 (8690), 662 (1990)} and Adult Respiratory Distress Syndrome where TNFα concentration in excess of 12,000 pg/mL have been detected in pulmonary aspirates from ARDS patients {Millar et al., *Lancet* 2(8665), 712–714 (1989)}. Systemic infusion of recombinant TNFα also resulted in changes typically seen in ARDS {Ferrai-Baliviera et al., *Arch. Surg.* 124(12), 1400–1405 (1989)}.

TNFα appears to be involved in bone resorption diseases, including arthritis. When activated, leukocytes will produce bone-resorption, an activity to which the data suggest TNFα contributes. {Bertolini et al., *Nature* 319, 516–518 (1986) and Johnson et al., *Endocrinology* 124(3), 1424–1427 (1989).} TNFα also has been shown to stimulate bone resorption and inhibit bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {*Calci. Tissue Int.* (US) 46(Suppl.), S3–10 (1990)}. In Graft versus Host Reaction, increased serum TNFα levels have been associated with major complication following acute allogenic bone marrow transplants {Holler et al., *Blood*, 75(4), 1011–1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., *N. Engl. J. Med.* 320(24), 1586–1591 (1989)}.

Macrophage-induced angiogenesis TNFα is known to be mediated by TNFα. Leibovich et al. {*Nature*, 329, 630–632 (1987)} showed TNFα induces in vivo capillary blood vessel formation in the rat cornea and the developing chick chorioallantoic membranes at very low doses and suggest TNFα is a candidate for inducing angiogenesis in inflammation, wound repair, and tumor growth. TNFα production also has been associated with cancerous conditions, particularly induced tumors {Ching et al., *Brit. J. Cancer*, (1955) 72, 339–343, and Koch, *Progress in Medicinal Chemistry*, 22, 166–242 (1985)}.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., *Nature*, 344, 245–247 (1990)}. High levels of TNFα production (in the serum and in isolated macrophages) have been demonstrated in animal models of silica and asbestos induced fibrosis {Bissonnette et al., *Inflammation* 13(3), 329–339 (1989)}. Alveolar macrophages from pulmonary sarcoidosis patients have also been found to spontaneously release massive quantities of TNFα as compared with macrophages from normal donors {Baughman et al., *J. Lab. Clin. Med.* 115(1), 36–42 (1990)}.

TNFα is also implicated in the inflammatory response which follows reperfusion, called reperfusion injury, and is a major cause of tissue damage after loss of blood flow {Vedder et al., *PNAS* 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., *J. Cell Biol.* 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., *Am. J. Path.* 135(1), 121–132 (1989)}.

TNFα blockage with monoclonal anti-TNFα antibodies has been shown to be beneficial in rheumatoid arthritis {Elliot et al., *Int. J. Pharmac.* 1995 17(2), 141–145}. High levels of TNFα are associated with Crohn's disease {von Dullemen et al., *Gastroenterology*, 1995 109(1), 129–135} and clinical benefit has been achieved with TNFα antibody treatment.

Moreover, it now is known that TNFα is a potent activator of retrovirus replication including activation of HIV-1. {Duh et al., *Proc. Nat. Acad. Sci.* 86, 5974–5978 (1989); Poll et al., *Proc. Nat. Acad. Sci.* 87, 782–785 (1990); Monto et al., *Blood* 79, 2670 (1990); Clouse et al., *J. Immunol.* 142, 431–438 (1989); Poll et al., *AIDS Res. Hum. Retrovirus*, 191–197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for viral replication and the level of viral replication is dependent upon the activation state of the cells. {Rosenberg et al., *The Immunopathogenesis of HIV Infection*, Advances in Immunology, 57 (1989)}. Cytokines, such as TNFα, have been shown to activate HIV replication in monocytes and/or macrophages {Poli et al., *Proc. Natl. Acad. Sci.*, 87, 782–784 (1990)}, therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of sells (Osborn, et al., *PNAS* 86 2336–2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., *PNAS* 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., *PNAS* 86, 2336–2340 (1989)}. TNFα in AIDS associated cachexia is suggested by elevated serum TNFα and high levels of spontaneous TNFα production in peripheral blood monocytes from patients {Wright et al., *J. Immunol.* 141(1), 99–104 (1988)}. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., *Cell* 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al., *J. Biol. Chem.* 1993, 17762–66; Duh et al., *Proc. Natl. Acad. Sci.* 1989, 86, 5974–78; Bachelerie et al., *Nature* 1991, 350, 709–12; Boswas et al., *J. Acquired Immune Deficiency Syndrome* 1993, 6, 778–786; Suzuki et al., *Biochem. And Biophys. Res. Comm.* 1993, 193, 277–83; Suzuki et al., *Biochem. And Biophys. Res Comm.* 1992, 189, 1709–15; Suzuki et al., *Biochem. Mol. Bio. Int.* 1993, 31(4), 693–700; Shakhov et al., *Proc. Natl. Acad. Sci. USA* 1990, 171, 35–47; and Staal et al., *Proc. Natl. Acad. Sci. USA* 1990, 87, 9943–47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, *Drugs of the Future*, 17(9), 799–807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle. Phosphodiesterases control the level of cAMP through hydrolysis and inhibitors of phosphodiesterases have been shown to increase cAMP levels.

Decreasing TNFα levels and/or increasing cAMP levels thus constitutes a valuable therapeutic strategy for the treatment of many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury. Prior efforts directed to the suppression of the effects of TNFα have ranged from the utilization of steroids such as dexamethasone and prednisolone to the use of both polyclonal and monoclonal antibodies {Beutler et al., *Science* 234, 470–474 (1985); WO 92/11383}.

Matrix metalloproteinase (MMP) inhibition has been associated with inhibition of TNF. Mohler et al., *Nature*, 370, 218–220 (1994). MMPs, or matrixins, are a family of secreted and membrane-bound zinc endopeptidases that play a key role in both physiological and pathological tissue degradation. See Yu et al., *Drugs & Aging*, 1997, (3):229–244; Wojtowicz-Praga et al., *Int. New Drugs*, 16:61–75 (1997). These enzymes are capable of degrading the components of the extracellular matrix, including fibrillar and non-fibrillar collagens, fibronectin, laminin, and membrane glycoproteins. Ordinarily, there is a delicate balance between cell division, matrix synthesis, and matrix degradation (under the control of cytokines), growth factors, and cell matrix interactions. Under pathological conditions, however, this balance can be disrupted. Conditions and diseases associated with undesired MMP levels include, but are not limited to, tumor metastasis, invasion, and growth, rheumatoid arthritis, osteoarthritis, osteopenias such as osteoporosis, periodontitis, gingivitis, and corneal epidermal or gastric ulceration.

Increased MMP activity has been detected in a wide range of cancers, Denis et al., *Invest. New Drugs*, 15:175–185 (1987), and as with TNF, MMPs are believed to be involved in the invasive processes of angiogenesis and tumor metastasis.

DETAILED DESCRIPTION

The present invention is based on the discovery that certain classes of non-polypeptide compounds more fully described herein decrease the levels of TNFα, increase cAMP levels, and inhibit phosphodiesterase.

In particular, the invention pertains to
(a) compounds of the formula:

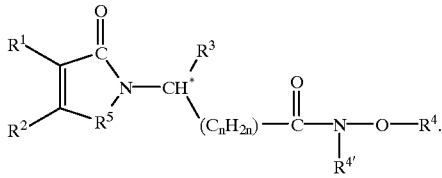

I wherein
each of $R^1$ and $R^2$, when taken independently of each other, is hydrogen, lower alkyl, or $R^1$ and $R^2$, when taken together, together with the depicted carbon atoms to which each is bound, is o-phenylene, o-naphthylene, or cyclohexene-1,2-diyl, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, and halo;

$R^3$ is phenyl substituted with from one to four substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, alkylthio of 1 to 10 carbon atoms, benzyloxy, cycloalkoxy of 3 to 6 carbon atoms, $C_4$-$C_6$-cycloalkylidenemethyl, $C_3$-$C_{10}$-alkylidenemethyl, indanyloxy, and halo;

$R^4$ is hydrogen, alkyl of 1 to 6 carbon atoms, phenyl, or benzyl;

$R^{4'}$ is hydrogen or alkyl of 1 to 6 carbon atoms;

$R^5$ is —$CH_2$—, —$CH_2$—CO—, —CO—, —$SO_2$—, —S—, or —NHCO—; and n has a value of 0, 1, or 2; and (b) the acid addition salts of said compounds which contain a nitrogen atom capable of being protonated.

Unless otherwise defined, the term alkyl denotes a univalent saturated branched or straight hydrocarbon chain containing from 1 to 8 carbon atoms. Representative of such alkyl groups are methyl, ethyl, propyl, isopropyl, butyl, isobutyl, sec-butyl, and tert-butyl. Alkoxy refers to an alkyl group bound to the remainder of the molecule through an ethereal oxygen atom. Representative of such alkoxy groups are methoxy, ethoxy, propoxy, isopropoxy, butoxy, isobutoxy, sec-butoxy, and tert-butoxy.

The compounds of Formula I are used, under the supervision of qualified professionals, to inhibit the undesirable effects of TNFα and inhibit phosphodiesterase. The compounds can be administered orally, rectally, or parenterally, alone or in combination with other therapeutic agents including antibiotics, steroids, etc., to a mammal in need of treatment.

The compounds of the present invention also can be used topically in the treatment or prophylaxis of topical disease states mediated or exacerbated by excessive TNFα production, respectively, such as viral infections, such as those caused by the herpes viruses, or viral conjunctivitis, psoriasis, atopic dermatitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

The invention also relates to MMP-inhibiting compounds, compositions thereof, and their use in the treatment of diseases and disorders associated with undesired production or activity of MMPs. These compounds are capable of inhibiting connective tissue breakdown, and are useful in the treatment or prevention of conditions involving tissue breakdown. These include, but are not limited to, tumor metastasis, invasion, and growth, rheumatoid arthritis, osteoarthritis, osteopenias such as osteoporosis, periodontitis, gingivitis, and corneal epidermal or gastric ulceration.

The invention thus further comprises MMP-inhibiting compounds of Formula I, and methods of treatment comprising administering an effective amount of a compound according to Formula I.

The compounds of Formula I are readily prepared by reacting a carboxylic acid of the formula:

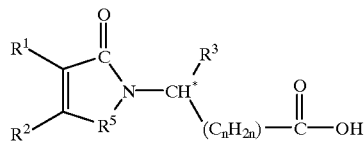

II in which each of $R^1$, $R^2$, $R^3$, $R^5$, and n are as defined above, with hydroxylamine hydrochloride or alkoxyamine hydrochloride in the presence of a coupling agent. The reaction generally is conducted in an inert solvent such as tetrahydrofuran under an inert atmosphere such as nitrogen. Ambient temperatures can be employed. When the reaction is substantially complete, the products can be readily isolated simply through the addition of water.

The compounds of Formula II which are here utilized as intermediates are described in U.S. Pat. No. 5,605,914, the disclosure of which is incorporated herein by reference. Briefly, such intermediates can be prepared through the reaction of an amino acid of the formula:

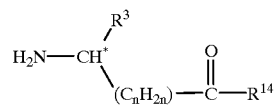

III in which $R^{14}$ is hydroxy or a protecting group, with an acid anhydride, an N-carbethoxyimide, a dialdehyde, or an o-bromo aromatic acid.

Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed at a later stage of the synthesis and compounds bearing such protecting groups thus are of importance primarily as chemical intermediates (although some derivatives also exhibit biological activity).

Accordingly the precise structure of the protecting group is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol. 15/I, Georg Thieme Verlag, Stuttgart 1974, the disclosures of which are incorporated herein by reference.

In any of the foregoing reactions, a nitro compound can be employed with the nitro group being converted to an amino group by catalytic hydrogenation. Alternatively, a protected amino group can be cleaved to yield the corresponding amino compound. An amino group can be protected as an amide utilizing an acyl group which is selectively removable under mild conditions, especially benzyloxycarbonyl, formyl, or a lower alkanoyl group which is branched in 1- or α position to the carbonyl group, particularly tertiary alkanoyl such as pivaloyl, a lower alkanoyl group which is substituted in the position α to the carbonyl group, as for example trifluoroacetyl.

The compounds of Formula I possess at least one center of chirality (designated by "*") and can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral absorbant. Alternatively, the individual isomers can be prepared in chiral form or separated chemically from a mixture by forming salts with a chiral acid or base, such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

The present invention also pertains to the physiologically acceptable non-toxic acid addition salts of the compound of Formula I. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The present invention also pertains to the physiologically acceptable non-toxic salts of the compound of Formula I with bases such as the sodium salt, the potassium salt, the aluminum salt, and the like.

A first preferred subgroup encompasses compounds of the formula:

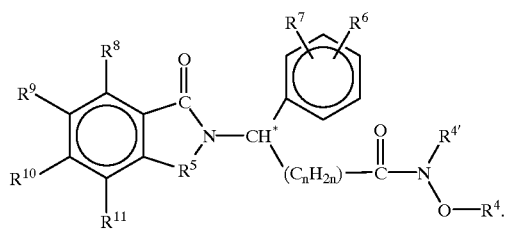

in which
$R^4$ is hydrogen or alkyl of 1 to 4 carbon atoms;
$R^{4'}$ is hydrogen or alkyl of 1 to 4 carbon atoms;
$R^5$ is C=O or $CH_2$;
each of $R^6$ and $R^7$, independently of the other, is nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, cylcoalkoxy of 3 to 6 carbon atoms, bicycloalkyl of 6 to 10 carbon atoms, indanyloxy, $C_4$–$C_6$-cycloalkylidenemethyl, $C_3$–$C_{10}$-alkylidenemethyl, or halo;
each of $R^8$, $R^9$, $R^{10}$, and $R^{11}$, independently of the others, is hydrogen, nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, and halo; and
n has a value of 1.

Among the compounds of Formula IV, those in which each of $R^8$, $R^9$, $R^{10}$, and $R^{11}$ is hydrogen, halo, alkyl of 1 to 4 carbon atoms, or alkoxy of 1 to 4 carbon atoms, and those in which one of $R^8$, $R^9$, $R^{10}$, and $R^{11}$ is amino, hydroxy, or methyl, and the remaining of $R^8$, $R^9$, $R^{10}$, and $R^{11}$, are hydrogen are particularly preferred.

A further preferred subgroup encompasses compounds of the formula:

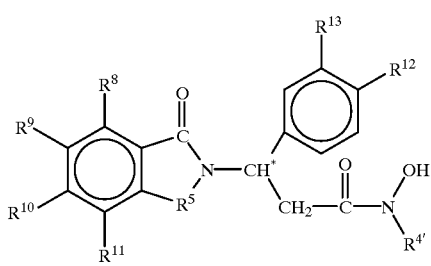

in which
$R^{4'}$ is hydrogen or alkyl of 1 to 4 carbon atoms;
$R^5$ is C=O or $CH_2$;
each of $R^{12}$ and $R^{13}$, independently of the other alkoxy of 1 to 4 carbon atoms, cylcoalkoxy of 3 to 6 carbon atoms; $C_4$–$C_6$-cycloalkylidenemethyl, $C_3$–$C_{10}$-alkylidenemethyl, or indanyloxy; and
each of $R^8$, $R^9$, $R^{10}$, and $R^{11}$, independently of the others, is hydrogen, nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, and halo.

Among the compounds of Formula V, those in which each of $R^8$, $R^9$, $R^{10}$, and $R^{11}$ is hydrogen, halo, alkyl of 1 to 4 carbon atoms, or alkoxy of 1 to 4 carbon atoms, and those in which one of $R^8$, $R^9$, $R^{10}$, and $R^{11}$ is amino or hydroxy and the remaining of $R^8$, $R^9$, $R^{10}$, and $R^{11}$, are hydrogen are particularly preferred.

Particularly preferred compounds include 3-(3-ethoxy-4-methoxyphenyl)-N-hydroxy-3-(1-oxoisoindolinyl) propionamide, 3-(3-ethoxy-4-methoxyphenyl)-N-methoxy-3-(1-oxoisoindolinyl)propionamide, N-benzyloxy-3-(3-ethoxy-4-methoxyphenyl)-3-phthalimidopropionamide, N-benzyloxy-3-(3-ethoxy-4-methoxyphenyl)-3-(3-nitrophthalimido)propionamide, N-benzyloxy-3-(3-ethoxy-4-methoxyphenyl)-3-(1-oxoisoindolinyl)propionamide, 3-(3-ethoxy-4-methoxyphenyl)-N-hydroxy-3-phthalimidopropionamide, N-hydroxy-3-(3,4-dimethoxyphenyl)-3-phthalimidopropionamide, 3-(3-ethoxy-4-methoxyphenyl)-N-hydroxy-3-(3-nitrophthalimido)propionamide, N-hydroxy-3-(3,4-dimethoxyphenyl)-3-(1-oxoisoindolinyl)propionamide, 3-(3-ethoxy-4-methoxyphenyl)-N-hydroxy-3-(4-methylphthalimido)propionamide, 3-(3-cyclopentyloxy-4-methoxyphenyl)-N-hydroxy-3-phthalimidopropionamide, 3-(3-ethoxy-4-methoxyphenyl)-N-hydroxy-3-(1,3-dioxo-2,3-dihydro-1H-benzo[f]isoindol-2-yl)propionamide, N-hydroxy-3-{3-(2-propoxy)-4-methoxyphenyl}-3-phthalimidopropionamide, 3-(3-ethoxy-4-methoxyphenyl)-3-(3,6-difluorophthalimido)-N-hydroxypropionamide, 3-(4-aminophthalimido)-3-(3-ethoxy-4-methoxyphenyl)-N-hydroxypropionamide, 3-(3-aminophthalimido)-3-(3-ethoxy-4-methoxyphenyl)-N-hydroxypropionamide, N-hydroxy-3-(3,4-dimethoxyphenyl)-3-(1-oxoisoindolinyl) propionamide, 3-(3-cyclopentyloxy-4-methoxyphenyl)-N-hydroxy-3-(1-oxoisoindolinyl)propionamide, and N-benzyloxy-3-(3-ethoxy-4-methoxyphenyl)-3-(3-nitrophthalimido)propionamide.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of Formulas I associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

Enzyme-linked immunosorbent assays for TNFα can be performed in a conventional manner. PBMC is isolated from normal donors by Ficoll-Hypaque density centrifugation. Cells are cultured in RPMI supplemented with 10% AB+ serum, 2 mM L-glutamine, 100 U/mL penicillin, and 100 mg/mL streptomycin. Drugs are dissolved in dimethylsulfoxide (Sigma Chemical) and further dilutions are done in supplemented RPMI. The final dimethylsulfoxide concentration in the presence or absence of drug in the PBMC suspensions is 0.25 wt %. Drugs are assayed at half-log dilutions starting at 50 mg/mL. Drugs are added to PBMC ($10^6$ cells/mL) in 96 wells plates one hour before the addition of LPS. PBMC ($10^6$ cells/mL) in the presence or absence of drug are stimulated by treatment with 1 mg/mL of LPS from *Salmonella minnesota* R595 (List Biological Labs, Campbell, Calif.). Cells are then incubated at 37° C. for 18–20 hours. Supernatants are harvested and assayed immediately for TNFα levels or kept frozen at −70° C. (for not more than 4 days) until assayed. The concentration of TNFα in the supernatant is determined by human TNFα ELISA kits (ENDOGEN, Boston, Mass.) according to the manufacturer's directions.

Phosphodiesterase can be determined in conventional models. For example, using the method of Hill and Mitchell, U937 cells of the human promonocytic cell line are grown to $1 \times 10^6$ cells/mL and collected by centrifugation. A cell pellet of $1 \times 10^9$ cells is washed in phosphate buffered saline and then frozen at −70° C. for later purification or immediately lysed in cold homogenization buffer (20 mM Tris-HCl, pH 7.1, 3 mM 2-mercaptoethanol, 1 mM magnesium chloride, 0.1 mM ethylene glycol-bis-(β-aminoethyl ether)-N,N,N',N'-tetraacetic acid (EGTA), 1 μM phenylmethylsulfonyl fluoride (PMSF), and 1 μg/mL leupeptin). Cells are homogenized with 20 strokes in a Dounce homogenizer and supernatant containing the cytosolic fraction are obtained by centrifugation. The supernatant then is loaded onto a Sephacryl S-200 column equilibrated in homogenization buffer. Phosphodiesterase is eluted in homogenization buffer at a rate of approximately 0.5 mL/min and fractions are assayed for phosphodiesterase activity −/+ rolipram. Fractions containing phosphodiesterase activity(rolipram sensitive) are pooled and aliquoted for later use.

The phosphodiesterase assay is carried out based on procedure described by Hill and Mitchell. The assay is carried out in a total volume of 100 μl containing various concentration of Celgene compounds, 50 mM Tris-HCl, pH 7.5,5 mM magnesium chloride and 1 μM cAMP of which 1% was $^3$H cAMP. Reactions are incubated at 30° C. for 30 minutes and terminated by boiling for 2 minutes. The amount of phosphodiesterase IV containing extract used for these experiments is predetermined such that reactions are within the linear range and consumed less than 15% of the total substrate. Following termination of reaction, samples are chilled at 4° C. and then treated with 10 μl 10 mg/mL snake venom for 15 min at 30° C. Unused substrate then is removed by adding 200 μl of a quaternary ammonium ion exchange resin (AG1-X8, BioRad) for 15 minutes. Samples then are spun at 3000 rpm, 5 min and 50 μl of the aqueous phase are taken for counting. Each data point is carried out in duplicate and activity is expressed as percentage of control. The $IC_{50}$ of the compound then is determined from dose response curves of a minimum of three independent experiments.

The following examples will serve to further typify the nature of this invention but should not be construed as a limitation in the scope thereof, which scope is defined solely by the appended claims.

EXAMPLE 1

3-(3-Ethoxy-4-methoxyphenyl)-N-hydroxy-3-(1-oxoisoindolinyl)propionamide

A mixture of 3-(3-ethoxy-4-methoxyphenyl)-3-(1-oxoisoindolinyl)propanoic acid (15.0 g, 42.7 mmol) and N,N'-carbonyldiimidazole (7.27 g, 44.8 mmol) in tetrahydrofuran (50 mL) under nitrogen was stirred at room temperature for 2 hours. To the resulting solution was added hydroxylamine hydrochloride (3.86 g, 55.5 mmol). The resulting suspension was stirred for 18 hours. To the suspension was added water (150 mL) and stirring was continued for 1 hour. The suspension was filtered, the solid was washed with water (5×30 mL) and ether (2×20 mL), and then was dried in a vacuum oven overnight (60° C., <1 torr) to give 3-(3-ethoxy-4-methoxyphenyl)-N-hydroxy-3-(1-oxoisoindolinyl)propionamide as a white solid (13.0 g, 82% yield): mp, 167–168° C.; $^1$H NMR (DMSO-$d_6$) δ1.29 (t, J=6.9 Hz, 3H, $CH_3$) 2.81–2.86 (m, 2H, $CH_2$), 3.72 (s, 3H, $CH_3$), 3.96–4.04 (m, 2H, $CH_2$), 4.13 (d, J=17.5 Hz, 1H, CHH), 4.54 (d, J=17.5 Hz, 1H, NCHH), 5.73 (t, J=7.9 Hz, 1H, NCH), 6.84–6.92 (m, 3H, Ar), 7.43–7.68 (m, 4H, Ar), 8.83 (br.s, 1H, OH), 10.61 (br s, 1H, NH); $^{13}$C NMR (DMSO-$d_6$) δ 14.68, 35.04, 46.22, 51.20, 55.44, 63.73, 111.85, 112.19, 119.21, 122.78, 123.43, 127.83, 131.29, 131.85, 132.27, 141.67, 147.85, 148.42, 165.99, 166.82. Anal. Calcd for $C_{20}H_{22}N_2O_5$: C, 64.85; H, 5.99; N, 7.56. Found: C, 64.73; H, 6.17; N, 7.36.

In a similar fashion, 3-(3-cyclopentyloxy-4-methoxyphenyl)-N-hydroxy-3-(4-methylphthalimido) propionamide was prepared from 3-(3-cyclopentyloxy-4-methoxyphenyl)-N-hydroxy-3-(4-methylphthalimido) propanoic acid (2.0 g, 4.7 mmol), carbonyl diimidazole (842 mg, 5.19 mmol) and hydroxylamine hydrochloride (426 mg, 6.13 mmol) in tetrahydrofuran (10 mL). The product is a white solid (1.34 g, 65% yield): mp, 112.0–116.0° C.; $^1$H NMR (DMSO-$d_6$) δ1.56–1.87 (m, 8H, $C_5H_8$), 2.47 (s, 3H, $CH_3$), 3.09 (d, J=7.8 Hz, 2H, $CH_2$), 3.70 (s, 3H, $CH_3$), 4.71–4.74 (m, 1H, OCR), 5.65 (t, J=7.8 Hz, 1H, NCH), 6.88 (br s, 2H, Ar), 7.01 (br s, 1H, Ar), 7.61–7.76 (m, 3H, Ar), 8.79 (br s, 1H, OH), 10.59 (br s, 1H, NH); $^{13}$C NMR (DMSO-$d_6$) δ21.34, 23.53, 32.19, 34.29, 50.12, 55.54, 79.56, 112.06, 114.10, 119.65, 123.05, 123.53, 128.62, 131.27, 131.60, 134.92, 145.58, 146.72, 149.13, 166.03, 167.64, 167.75; Anal Calcd for $C_{24}H_{26}N_2O_6$ 1.2$H_2O$: C, 62.65; H, 6.22; N, 6.09. Found: C, 62.56; H, 6.12; N, 5.87.

EXAMPLE 2

3-(3-Ethoxy-4-methoxyphenyl)-N-hydroxy-3-(4-methylphthalimido)propionamide

A. A stirred solution of 3-amino-3-(3-ethoxy-4-methoxyphenyl)propanoic acid (3.00 g, 12.5 mmol) and 4-methylphthalic anhydride (2.13 g, 12.5 mmol, 95%) in acetic acid was heated to reflux under nitrogen for 18 hours. The mixture was allowed to cool to room temperature. The solvent was removed in vacuo to give an oil. The resulting oil was stirred with ethyl acetate (10 mL), hexane (10 mL) and water (30 mL) for 30 minutes. The resulting suspension was filtered. The solid was washed with water (3×10 mL) and hexane (3×10 mL), and then was dried in a vacuum oven overnight (60° C., <1 torr) to give 3-(3-ethoxy-4-methoxyphenyl)-3-(4-methylphthalimido)propanoic acid as a white solid (3.4 g, 71% yield): mp, 134.0–136.0° C.; $^1$H NMR (DMSO-$d_6$) δ1.31 (t, J=6.9 Hz, 3H, $CH_3$), 2.47 (s, 3H, $CH_3$), 3.23 (dd, J=6.7, 16.5 Hz, 1H, CHH), 3.50 (dd, J=9.2, 16.5 Hz, 1H, CHH), 3.72 (s, 3H, $CH_3$), 3.97 (q, J=6.9 Hz, 2H, $CH_2$), 5.58 (dd, J=6.7, 9.1 Hz, 1H, NCH), 6.90–6.95 (m, 2H, Ar), 7.01 (br s, 1H, Ar), 7.61–7.76 (m, 3H, Ar), 12.4 (br s, 1H, OH); $^{13}$C NMR (DMSO-$d_6$) δ14.65, 21.32, 36.09, 50.04, 55.45, 63.72, 111.79, 112.15, 119.29, 123.08, 123.58, 128.51, 131.35, 131.49, 134.95, 145.63, 147.75, 148.53, 167.67, 167.78, 171.72; Anal Calcd for $C_{21}H_{21}NO_6$: C, 65.79; H, 5.52; N, 3.65. Found: C, 65.46; H, 5.57; N, 3.31.

B. 3-(3-Ethoxy-4-methoxyphenyl)-N-hydroxy-3-(4-methylphthalimido)propionamide was prepared by the procedure of Example 1 from 3-(3-ethoxy-4-methoxyphenyl)-3-(4-methyl-phthalimido)propanoic acid (2.40 g, 6.26 mmol), N,N'-carbonyldiimidazole (1.12 g, 6.91 mmol) and hydroxylamine hydrochloride (530 mg, 7.62 mmol) in tetrahydrofuran (8 mL) to afford 3-(3-ethoxy-4-methoxyphenyl)-N-hydroxy-3-(4-methylphthalimido)-propionamide as a white solid (2.19 g, 88% yield): mp, 180.0–181.5° C.; $^1$H NMR (DMSO-$d_6$) δ1.31 (t, J=6.9 Hz, 3H, $CH_3$), 2.49 (s, 3H, $CH_3$), 3.09 (d, J=7.9 Hz, 2H, $CH_2$), 3.71 (s, 3H, $CH_3$), 3.97 (q, J=7.0 Hz, 2H, $CH_2$), 5.65 (t, J=7.9 Hz, 1H, NCR), 6.89 (br s, 2H, Ar), 7.01 (br s, 1H, Ar), 7.61–7.74 (m, 3H, Ar), 8.78 (br s, 1H, OH), 10.57 (br s, 1H, NH); $^{13}$C NMR (DMSO-$d_6$) δ14.67, 21.33, 34.31, 50.14, 55.45, 63.72, 111.75, 112.33, 119.61, 123.03, 123.52, 128.63, 131.32, 131.61, 134.88, 145.54, 147.67, 148.52, 166.02, 167.62, 167.73; Anal Calcd for $C_{21}H_{22}N_2O_6$: C, 63.31; H, 5.57; N, 7.03. Found: C, 63.29; H, 5.69; N, 6.86.

EXAMPLE 3

3-(3-Cyclopentyloxy-4-methoxyphenyl)-N-hydroxy-3-phthalimidopropionamide

A. A mixture of 3-amino-3-(3-cyclopentyloxy-4-methoxyphenyl)propanoic acid (3.00 g, 10.8 mmol) and sodium carbonate (1.20 g, 11.3 mmol) in acetonitrile (30 mL) and water (30 mL) under nitrogen was stirred at room temperature for 15 minutes. To the resulting solution was added N-ethoxycarbonyl phthalimide (2.36 g, 10.8 mmol). The resulting mixture was stirred at room temperature for 18 hours. Most of solvent was removed in vacuo. To the solution was added hydrochloric acid (6N) until the pH of solution <1 to give a suspension and stirring was continued for 1 hour. The suspension was filtered, the solid was washed with water (2×10 mL), and then was dried in a vacuum oven overnight (60° C., <1 torr) to afford 3-(3-cyclopentyloxy-4-methoxyphenyl)-3-phthalimidopropanoic acid as a white solid (3.0 g, 68% yield): mp, 168.0–169.0° C.; $^1$H NMR (DMSO-$d_6$) δ1.55–1.88 (m, 8H, $C_5H_8$), 3.27 (dd, J=6.9, 16.5 Hz, 1H, CHH), 3.51 (dd, J=8.9, 16.5 Hz, 1H, CHH), 3.71 (s, 3H, $CH_3$), 4.71–4.75 (m, 1H, CH), 5.61 (dd, J=6.9, 8.8 Hz, 1H, NCH), 6.87–6.95 (m, 2H, Ar), 7.03 (br s, 1H, Ar), 7.81–7.91 (m, 4H, Ar), 12.4 (br s, 1H, OH); $^{13}$C NMR (DMSO-$d_6$) δ23.51, 32.14, 32.17, 36.07, 50.08, 55.52, 79.57, 112.15, 113.97, 119.39, 123.17, 131.09, 131.19, 134.66, 146.77, 149.16, 167.67, 171.72; Anal Calcd for $C_{23}H_{23}NO_6$: C, 67.47; H, 5.66; N, 3.42. Found: C, 67.21; H, 5.46; N, 3.45.

B. 3-(3-Cyclopentyloxy-4-methoxyphenyl)-N-hydroxy-3-phthalimidopropionamide was prepared by the procedure of Example 1 from 3-(3-cyclopentyloxy-4-methoxyphenyl)-3-phthalimidopropanoic acid (1.50 g, 3.67 mmol), N,N'-carbonyldiimidazole (653 mg, 4.03 mmol) and hydroxylamine hydrochloride (308 mg, 4.43 mmol) in tetrahydrofuran (5 mL) to afford 3-(3-cyclopentyloxy-4-methoxyphenyl)-N-hydroxy-3-phthalimidopropionamide as a white solid (1.45 g, 93% yield): mp, 169.0–171.0° C.; $^1$H NMR (DMSO-d$_6$) δ1.54–1.85 (m, 8H, C$_5$H$_8$), 3.09 (d, J=7.9 Hz, 2H, CH$_2$), 3.69 (s, 3H, CH$_3$), 4.70–4.72 (m, 1H, CH), 5.67 (t, J=7.9 Hz, 1H, NCH), 6.87 (br s, 2H, Ar), 7.01 (br s, 1H, Ar), 7.79–7.87 (m, 4H, Ar), 8.78 (br s, 1H, OH), 10.58 (1H, NH); $^{13}$C NMR (DMSO-d$_6$) δ23.51, 32.17, 34.23, 50.19, 55.53, 79.57, 112.08, 114.16, 119.69, 123.11, 131.16, 131.20, 134.59, 146.73, 149.17, 166.01, 167.63; Anal Calcd for C$_{23}$H$_{24}$N$_2$O$_6$: C, 65.08; H, 5.70; N, 6.60. Found: C, 64.73; H, 5.60; N, 6.53.

EXAMPLE 4

N-Hydroxy-N-methyl-3-(3-ethoxy-4-methoxyphenyl)-3-(1-oxoisoindolinyl)propionamide N-Hydroxy-3-(3-ethoxy-4-methoxyphenyl)-3-(1-oxoisoindolinyl)propionamide was prepared by the procedure of Example 1 from 3-(3-ethoxy-4-methoxyphenyl)-3-(1-oxoisoindolinyl)propanoic acid (1.0 g, 2.8 mmol), carbonyldiimidazole (500 mg, 3.1 mmol) and N-methylhydroxylamine hydrochloride (300 mg, 3.5 mmol) in tetrahydrofuran (10 mL) to afford N-hydroxy-N-methyl-3-(3-ethoxy-4-methoxyphenyl)-3-(1-oxoisoindolinyl) propionamide as a white solid (650 mg, 61% yield): mp, 122.0–124.5° C.; $^1$H NMR(CDCl$_3$) δ1.43 (t, J=7.0 Hz, 3H, CH$_3$), 3.14 (s, 3H, NCH$_3$), 3.37–3.48 (m, 2H, CH$_2$), 3.86 (s, 3H, CH$_3$), 4.02 (q, J=7.0 Hz, 2H, CH$_2$), 4.11 (d, J=17.2 Hz, NCHH), 4.51 (d, J=17.2 Hz, 1H, NCHH), 5.95 (dd, J=6.5, 10.9 Hz, 1H, NCH), 6.83–6.97 (m, 3H, Ar), 7.34–7.55 (m, 3H, Ar), 7.81 (d, J=7.1 Hz, 1H, Ar), 9.44 (br s, 1H, OH); $^{13}$C NMR (DMSO-d$_6$) δ14.71, 36.04, 38.11, 48.14, 52.36, 55.95, 64.52, 111.42, 112.42, 119.45, 122.95, 123.63, 128.06, 130.57, 131.88, 141.72, 148.65, 149.18, 170.00, 170.17; Anal Calcd for C$_{21}$H$_{24}$N$_2$O$_5$: C, 65.61; H, 6.29; N, 7.29. Found: C, 65.56; H, 6.26; N, 7.09.

EXAMPLE 5

3-(3-Cyclopentyloxy-4-methoxyphenyl)-N-hydroxy-3-(4-methylphthalimido)propionamide 3-(3-Cyclopentyloxy-4-methoxyphenyl)-N-hydroxy-3-(4-methylphthalimido)propionamide was prepared by the procedure of Example 1 from 3-(3-cyclopentyloxy-4-methoxyphenyl)-N-hydroxy-3-(4-methylphthalimido) propanoic acid (2.0 g, 4.7 mmol), carbonyldiimidazole (842 mg, 5.19 mmol) and hydroxylamine hydrochloride (426 mg, 6.13 mmol) in tetrahydrofuran (10 mL) to afford 3-(3-cyclopentyloxy-4-methoxyphenyl)-N-hydroxy-3-(4-methylphthalimido)propionamide as a white solid (1.34 g, 65% yield): mp, 112.0–116.0° C.; $^1$H NMR (DMSO-d$_6$) δ1.56–1.87 (m, 8H, C$_5$H$_8$), 2.47 (s, 3H, CH$_3$), 3.09 (d, J=7.8 Hz, 2H, CH$_2$), 3.70 (s, 3H, CH$_3$), 4.71–4.74 (m, 1H, OCH), 5.65 (t, J=7.8 Hz, 1H, NCH), 6.88 (br s, 2H, Ar), 7.01 (br s, 1H, Ar), 7.61–7.76 (m, 3H, Ar), 8.79 (br s, 1H, OH), 10.59 (br s, 1H, NH); $^{13}$C NMR (DMSO-d$_6$) δ21.34, 23.53, 32.19, 34.29, 50.12, 55.54, 79.56, 112.06, 114.10, 119.65, 123.05, 123.53, 128.62, 131.27, 131.60, 134.92, 145.58, 146.72, 149.13, 166.03, 167.64, 167.75; Anal Calcd for C$_{24}$H$_{26}$N$_2$O$_6$ 1.2H$_2$O: C, 62.65; H, 6.22; N, 6.09. Found: C, 62.56; H, 6.12; N, 5.87.

EXAMPLE 6

3-(3-Ethoxy-4methoxyphenyl)-N-hydroxy-3-(1,3-dioxo-2,3-dihydro-1H-benzo[f]isoindol-2-yl) propionamide A. 3-(3-Ethoxy-4-methoxyphenyl)-3-(1,3-dioxo-2,3-dihydro-1H-benzo[f]isoindol-2-yl)-propanoic acid was prepared according to Example 2A from 3-amino-3-(3-ethoxy-4-methoxyphenyl)propanoic acid (3.00 g, 12.5 mmol), 2,3-napthalene dicarboxylic anhydride (2.59 g, 12.5 mmol) in acetic acid (20 mL) to afford 3-(3-ethoxy-4-methoxyphenyl)-3-(1,3-dioxo-2,3-dihydro-1H-benzo[f]isoindol-2-yl)propanoic acid as an off-white solid (4.9 g, 93% yield): mp, 193.0–194.0° C.; $^1$H NMR (DMSO-d$_6$) δ1.32 (t, J=6.9 Hz, 3H, CH$_3$), 3.34 (dd, J=7.1, 16 Hz, 1H, CHH), 3.57 (dd, J=8.9, 16 Hz, 1H, CHH), 3.74 (s, 3H, CH$_3$), 4.02 (q, J=6.9 Hz, 2H, CH$_2$), 5.71 (dd, J=7, 8 Hz, 1H, NCH), 6.91–6.98 (m, 2H, Ar), 7.09 (br s, 1H, Ar), 7.74–7.78 (m, 2H, Ar), 8.23–8.27 (m, 2H, Ar), 8.50 (br s, 2H, Ar), 12.5 (br s, 1H, OH); $^{13}$C NMR (DMSO-d$_6$) δ14.62, 36.03, 50.28, 55.43, 63.71, 111.79, 112.28, 119.45, 124.55, 126.87, 129.27, 130.24, 131.24, 135.03, 147.74, 148.57, 167.29, 171.75; Anal Calcd for C$_{24}$H$_{21}$NO$_6$: C, 68.73; H, 5.05; N, 3.34. Found: C, 68.59; H, 5.25; N, 3.17.

B. 3-(3-Ethoxy-4-methoxyphenyl)-N-hydroxy-3-(1,3-dioxo-2,3-dihydro-1H-benzo[f]-isoindol-2-yl)propionamide was prepared by the procedure of Example 1 from 3-(3-ethoxy-4-methoxyphenyl)-3-(1,3-dioxo-2,3-dihydro-1H-benzo[f]isoindol-2-yl)propanoic acid (2.00 g, 4.77 mmol), N,N'-carbonyldiimidazole (889 mg, 5.48 mmol) and hydroxylamine hydrochloride (419 mg, 6.03 mmol) in tetrahydrofuran (8 mL) to afford 3-(3-ethoxy-4-methoxyphenyl)-N-hydroxy-3-(1,3-dioxo-2,3-dihydro-1H-benzo[f]isoindol-2-yl)propionamide as an off-white solid (1.6 g, 77% yield): mp, 197.0–199.0° C.; $^1$H NMR (DMSO-d$_6$) δ1.33 (t, J=7.0 Hz, 3H, CH$_3$), 3.11–3.28 (m, 2H, CH$_2$), 3.73 (s, 3H, CH$_3$), 4.00 (q, J=7.0 Hz, 2H, CH$_2$), 5.79 (t, J=7.8 Hz, 1H, NCH), 6.87–7.09 (m, 2H, Ar), 7.10 (br s, 1H, Ar), 7.74–7.78 (m, 2H, Ar), 8.23–8.27 (m, 2H, Ar), 8.49 (br s, 1H, Ar), 8.85 (br s, 1H OH), 10.66 (br s, 1H, NH); $^{13}$C NMR (DMSO-d$_6$) δ14.69, 34.27, 50.42, 55.45, 63.73, 111.73, 112.45, 119.82, 124.50, 127.04, 129.28, 130.26, 131.20, 135.05, 147.69, 148.58, 166.07, 167.30; Anal Calcd for C$_{24}$H$_{22}$N$_2$O$_6$: C, 66.35; H. 5.10; N, 6.45. Found: C, 66.22; H, 5.24; N, 6.08.

EXAMPLE 7

3-(3-Ethoxy-4-methoxyphenyl)-N-methoxy-3-(1-oxoisoindolinyl)propionamide

A mixture of 3-(3-ethoxy-4-methoxyphenyl)-3-(1-oxoisoindolinyl)propanoic acid (500 mg, 1.41 mmol) and N,N'-carbonyldiimidazole (250 mg, 1.54 mmol) in methylene chloride (30 mL) under nitrogen was stirred at room temperature for 30 minutes. To the solution was added O-methyl hydroxylamine hydrochloride (175 mg, 2.09 mmol) followed by the addition of 1-methyl piperidine (0.26 mL, 2.14 mmol). The mixture was stirred at room temperature for 2 hours and then was heated to reflux for 14 hours. The cooled reaction mixture was washed with hydrochloric acid (1N, 25 mL), saturated sodium bicarbonate (25 mL), brine (25 mL), and then dried over sodium carbonate and sodium sulfate. Removal of solvent in vacuo gave a solid which was stirred with ether (10 mL) for 30 minutes. This suspension was filtered and the solid was washed with ether (2×10 mL) to give 3-(3-ethoxy-4-methoxyphenyl)-N- methoxy-3-(1-oxoisoindolinyl)-propionamide as a white solid (360 mg, 67% yield): mp, 138.0–139.5° C.; $^1$H NMR (CDCl$_3$) δ1.41 (t, J=6.9 Hz, 3H, CH$_3$), 2.95 (dd, J=4.6, 14.5 Hz, 1H, CHH), 3.53 (dd, J=11.2, 14.5 Hz, 1H, CHH), 3.62 (s, 3H, CH$_3$), 3.84 (s, 3H, CH$_3$), 4.02 (q, J=6.9 Hz, 2H, CH$_2$), 4.23 (d, J=17.1 Hz, 1H, NCHH), 4.46 (d, J=17 Hz, 1H, NCHH), 5.49 (dd, J=4.4, 10.3 Hz, 1H, NCH), 6.78–6.99 (m, 3H, Ar,), 7.27–7.51 (m, 3H, Ar), 7.78 (dd, J=7.4 Hz, 1H, Ar), 10.08 (br s, 1H, NH); 13C NMR (CDCl$_3$) δ14.66, 37.52, 49.48, 54.94, 5.91, 64.01, 64.41, 111.37, 112.12, 119.26, 122.75, 123.54, 128.04, 131.38, 131.68, 132.58, 141.44, 148.56, 149.15, 167.81, 169.47. Anal. Calcd for C$_{21}$H$_{24}$N$_2$O$_5$: C, 65.61; H, 6.29; N, 7.29. Found: C, 65.23; H, 6.52; N, 6.88.

EXAMPLE 8

N-Benzyloxy-3-(3-ethoxy-4-methoxyphenyl)-3-phthalimidopropionamide

N-Benzyloxy-3-(3-ethoxy-4-methoxyphenyl)-3-phthalimidopropionamide was prepared by the procedure of Example 1 from 3-(3-ethoxy-4-methoxyphenyl)-3-phthalimido-propanoic acid (869 mg, 2.36 mmol), N,N'-carbonyldiimidazole (410 mg, 2.53 mmol) and O-benzylhydroxylamine hydrochloride (444 mg, 2.78 mmol) in tetrahydrofuran (6 mL) to afford N-benzyloxy-3-(3-ethoxy-4-methoxyphenyl)-3-phthalimidopropionamide as a white solid (1.05 g, 94% yield): mp, 165.0–166.0° C.; $^1$H NMR (CDCl$_3$) δ1.44 (t, J=7.0 Hz, 3H, CH$_3$), 2.95 (dd, J=5.8, 14.0 Hz, 1H, CHH), 3.49 (t, J=12.1 Hz, 1H, CHH), 3.83 (s, 3H, CH$_3$), 4.07 (q, J=7.0 Hz, 2H, CH$_2$), 4.77 (br s, 2H, PhCH$_2$), 5.83 (dd, J=6.0, 10.0 Hz, 1H, NCH), 6.79 (d, J=8.0 Hz, 1H, Ar), 7.06–7.09 (m, 2H, Ar), 7.25–7.85 (m, 5H, Ar), 7.66–7.71 & 7.74–7.79 (2 ms, 4H, Ar), 8.34 (br s, 1H, NH); $^{13}$C NMR (CDCl$_3$) δ14.68, 35.66, 51.54, 55.88, 64.34, 78.13, 111.32, 12.52, 120.08, 123.29, 128.52, 128.67, 129.06, 131.26, 131.76, 133.98, 134.98, 148.31, 149.15, 167.38, 168.26. Anal. Calcd for C$_{27}$H$_{26}$N$_2$O$_6$: C, 68.34; H, 5.52; N, 5.90. Found: C, 68.36; H, 5.47; N, 5.74.

EXAMPLE 9

N-Benzyloxy-3-(3-ethoxy-4-methoxyphenyl)-3-(3-nitrophthalimido)propionamide

N-Benzyloxy-3-(3-ethoxy-4-methoxyphenyl)-3-(3-nitrophthalimido)propionamide was prepared by the procedure of Example 1 from 3-(3-ethoxy-4-methoxyphenyl)-3-(3-nitrophthalimido)propanoic acid (1.30 g, 3.14 mmol), N,N'-carbonyldiimidazole (533 mg, 3.28 mmol) and O-benzylhydroxylamine hydrochloride (550 mg, 3.45 mmol) in tetrahydrofuran (10 mL) to afford N-benzyloxy-3-(3-ethoxy-4-methoxyphenyl)-3-(3-nitrophthalimido) propionamide as a yellow solid (1.4 g, 86% yield): mp, 137.0–139.0° C.; $^1$H NMR (DMSO-d$_6$) δ1.30 (t, J=6.8 Hz, 3H, CH$_3$), 3.05–3.16 (m, 2H, CH$_2$), 3.72 (s, 3H, CH$_3$), 4.09 (q, J=6.8 Hz, 2H, CH$_2$), 4.64 (s, 2H, PhCH$_2$), 5.68 (t, J=7.8 Hz, 1H, NCR), 6.87–7.02 (m, 3H, Ar), 7.23–7.41 (m, 5H, Ar), 8.11 (d, J=8.1 Hz, 1H, Ar), 8.48 (s, 1H, Ar), 8.62 (dd, J=1.8, 8.2 Hz, 1H, Ar), 11.24 (br s, 1H, NH); $^{13}$C NMR (DMSO-d$_6$) δ14.64, 34.17, 50.76, 55.45, 63.71, 76.67, 111.68, 112.37, 118.02, 119.76, 124.70, 128.16, 128.62, 129.75, 130.42, 132.52, 135.74, 135.79, 147.73, 148.69, 151.50, 165.73, 165.99, 166.17. Anal. Calcd for C$_{27}$H$_{25}$N$_3$O$_8$: C, 62.42; H, 4.85; N, 8.09. Found: C, 62.34; H, 4.71; N, 8.05.

EXAMPLE 10

N-Benzyloxy-3-(3-ethoxy-4methoxyphenyl)-3-(1-oxoisoindolinyl)propionamide

N-Benzyloxy-3-(3-ethoxy-4-methoxyphenyl)-3-(1-oxoisoindolinyl)propionamide was prepared by the procedure of Example 1 from 3-(3-ethoxy-4-methoxyphenyl)-3-(1-oxoisoindolinyl)propanoic acid (1.78 g, 5.00 mmol), N,N'-carbonyldiimidazole (850 mg, 5.24 mmol) and O-benzylhydroxylamine hydrochloride (940 mg, 5.89 mmol) in tetrahydrofuran (10 mL) to afford N-benzyloxy-3-(3-ethoxy-4-methoxyphenyl)-3-(1-oxoisoindolinyl) propionamide as a white solid (1.73 g, 75% yield): mp, 132.0–133.0° C.; $^1$H NMR (DMSO-d$_6$) δ1.29 (t, J=6.9 Hz, 3H, CH$_3$), 2.83 (d, J=7.8 Hz, 2H, CH$_2$), 3.72 (s, 3H, CH$_3$), 3.93–4.02 (m, 2H, CH$_2$), 4.09 (d, J=17.5 Hz, 1H, NCHH), 4.51 (d, J=17.5 Hz, 1H, NCHH), 4.59 (d, J=11.3 Hz, 1H, PhCHH), 4.66 (d, J=11.2 Hz, 1H, PhCHH), 5.74 (t, J=7.8 Hz, 1H, NCH), 6.83–6.93 (m, 3H, Ar), 7.21–7.29 & 7.45–7.59 (m, 8H, Ar), 7.68 (d, J=7.4 Hz, 1H, Ar), 11.17 (br s, 1H, NH); $^{13}$C NMR (DMSO-d$_6$) δ14.66, 35.08, 46.18, 51.29, 55.43, 63.71, 76.69, 111.82, 112.11, 119.25, 122.82, 123.44, 127.85, 128.17, 128.75, 131.31, 131.61, 132.17, 135.86, 141.68, 147.88, 148.45, 166.26, 166.88. Anal. Calcd for C$_{27}$H$_{28}$N$_2$O$_5$: C, 70.42; H, 6.13; N, 6.08. Found: C, 70.31; H, 6.07; N, 5.88.

EXAMPLE 11

3-(3-Ethoxy-4-methoxyphenyl)-N-hydroxy-3-phthalimidopropionamide 3-(3-Ethoxy-4-methoxyphenyl)-N-hydroxy-3-phthalimidopropionamide was prepared by the procedure of Example 1 from 3-(3-ethoxy-4-methoxyphenyl)-3-phthalimidopropanoic acid (1.00 g, 2.71 mmol), N,N'-carbonyldiimidazole (461 mg, 2.84 mmol) and hydroxylamine hydrochloride (208 mg, 2.99 mmol) in tetrahydrofuran (6 mL) to afford 3-(3-ethoxy-4-methoxyphenyl)-N-hydroxy-3-phthalimidopropionamide as a white solid (800 mg, 77% yield): mp, 163.0–165.0° C.; $^1$H NMR (DMSO-d$_6$) δ 1.31 (t, J=6.9 Hz, 3H, CH$_3$), 3.11 (d, J=7.9 Hz, 2H, CH$_2$), 3.72 (s, 3H, CH$_3$), 3.97 (q, J=6.9 Hz, 2H, CH$_2$), 5.67 (t, J=7.8 Hz, 1H, NCH), 6.90 (br s, 2H, Ar), 7.02 (br s, 1H, Ar), 7.86 (br s, 4H, Ar), 8.79 (br s, 1H, OH), 10.59 (br s, 1H, NH); $^3$C NMR (DMSO-d$_6$) δ14.67, 34.22, 50.18, 55.44, 63.71, 111.73, 112.36, 119.65, 123.11, 131.18, 131.21, 134.56, 147.67, 148.53, 165.97, 167.61. Anal. Calcd for C$_{20}$H$_{20}$N$_2$O$_6$: C, 62.49; H, 5.24; N, 7.29. Found: C, 62.43; H, 5.04; N, 7.20.

EXAMPLE 12

N-Hydroxy-3-(3,4-dimethoxyphenyl)-3-phthalimidopropionamide

N-Hydroxy-3-(3,4-dimethoxyphenyl)-3-phthalimidopropionamide was prepared by the procedure of Example 1 from 3-(3,4-dimethoxyphenyl)-3-phthalimidopropanoic acid (1.82 g, 5.12 mmol), N,N'-carbonyldiimidazole (870 mg, 5.39 mmol) and hydroxylamine hydrochloride (391 mg, 5.63 mmol) in tetrahydrofuran (8 mL) to afford N-hydroxy-3-(3,4-dimethoxyphenyl)-3-phthalimidopropionamide as a white solid (1.52 g, 80% yield): mp, 186.5–188.0° C.; $^1$H NMR (DMSO-d$_6$) δ3.12 (d, J=7.8 Hz, 2H, CH$_2$), 3.72 (s, 3H, OCH$_3$), 3.74 (s, 3H, OCH$_3$), 5.69 (t, J=7.8 Hz, 1H, NCH), 6.91–6.92 (m, 2H, Ar), 7.03 (br s, 1H, Ar), 7.85 (br s, 4H, Ar), 8.82 (s, 1H, OH), 10.62 (br s, 1H, NH); $^{13}$C NMR (DMSO-d$_6$) δ34.33, 50.25, 55.52, 111.27, 111.67, 119.65, 123.17, 131.26, 134.63, 148.41, 148.56, 166.07, 167.69. Anal. Calcd for C$_{19}$H$_{18}$N$_2$O$_6$: C, 61.62; H, 4.90; N, 7.56. Found: C, 61.29; H, 4.72; N, 7.47.

EXAMPLE 13

3-(3-Ethoxy-4methoxyphenyl)-N-hydroxy-3-(3-nitrophthalimido)propionamide 3-(3-Ethoxy-4methoxyphenyl)-N-hydroxy-3-(3-nitrophthalimido)propionamide was prepared by the procedure of Example 1 from 3-(3-ethoxy-4-methoxyphenyl)-3-(3-nitrophthalimido)propanoic acid (3.64 g, 8.86 mmol), N,N'-carbonyldiimidazole (1.50 g, 9.25 mmol) and hydroxylamine hydrochloride (672 mg, 9.67 mmol) in tetrahydrofuran (20 mL) to afford 3-(3-ethoxy-4methoxyphenyl)-N-hydroxy-3-(3-nitrophthalimido)propionamide as a yellow solid (2.92 g, 77% yield): mp, 162.5–163.5° C.; $^1$H NMR (DMSO-d$_6$) δ1.31 (t, J=6.9 Hz, 3H, CH$_3$), 3.02 (dd, J=7.5, 14.8 Hz, 1H, CHH), 3.17 (dd, J=8.3, 14.8 Hz, 1H, CHH), 3.72 (s, 3H, CH$_3$), 4.00 (q, J=6.9 Hz, 2H, CH$_2$), 5.68 (t, J=7.7 Hz, 1H, NCH), 6.87–6.96 (m, 2H, Ar), 7.01 (br s, 1H, Ar), 8.05 (t, J=7.7 Hz, 1H, Ar), 8.15 (d, J=7.0 Hz, 1H, Ar), 8.27 (d, J=7.8 Hz, 1H, Ar), 8.82 (s, 1H, OH), 10.62 (br s, 1H, NH); $^{13}$C NMR (DMSO-d$_6$) δ14.66, 33.92, 50.59, 55.46, 63.74, 111.69, 112.59, 119.89, 122.48, 126.91, 128.43, 130.42, 133.13, 136.35, 144.33, 147.67, 148.67, 162.99, 165.70, 165.87. Anal. Calcd for C$_{20}$H$_{19}$N$_3$O$_8$+0.4 mole ethyl acetate: C, 55.83; H, 4.86; N, 8.96. Found: C, 55.86; H, 4.94; N, 8.73.

EXAMPLE 14

N-Hydroxy-3-{3-(2-propoxy)-4-methoxyphenyl}-3-phthalimidopropionamide

N-Hydroxy-3-{3-(2-propoxy)-4-methoxyphenyl}-3-phthalimidopropionamide was prepared by the procedure of Example 1 from 3-{3-(2-propoxy)-4-methoxyphenyl}-3-phthalimidopropanoic acid (2.0 g, 5.2 mmol), carbonyldiimidazole (1.02 g, 6.29 mmol), and hydroxylamine hydrochloride (481 mg, 6.92 mmol) in tetrahydrofuran (10 mL) to afford N-hydroxy-3-{3-(2-propoxy)-4-methoxyphenyl}-3-phthalimidopropionamide as a white solid (1.42 g, 68% yield): mp, 119.0–121.0° C.; $^1$H NMR (DMSO-d$_6$) δ1.24 (d, J=6.0 Hz, 3H, CH$_3$), 1.243 (d, J=6.0 Hz, 3H, CH$_3$), 3.12 (d, J=7.9 Hz, 2H, CH$_2$), 3.71 (s, 3H, CH$_3$), 4.45–4.51 (m, 1H, CH), 5.68 (t, J=7.9 Hz, 1H, NCH), 6.91 (br s, 2H, Ar), 7.05 (br s, 1H, Ar), 7.84–7.86 (m, 4H, Ar), 8.79 (br s, 1H, OH), 10.60 (1H, NH); $^{13}$C NMR (DMSO-d$_6$) δ21.80, 21.88, 34.19, 50.13, 55.49, 70.44, 112.18, 114.97, 120.12, 123.11, 131.13, 131.21, 134.59, 146.37, 149.51, 165.99, 167.62; Anal Calcd for C$_{21}$H$_{22}$N$_2$O$_6$0.9H$_2$O: C, 60.83; H, 5.79; N, 6.76. Found: C, 60.83; H, 5.73; N, 6.56; H$_2$O, 4.02.

EXAMPLE 15

3-(3-Ethoxy-4-methoxyphenyl)-3-(3,6-difluorophthalimido)-N-hydroxypropionamide 3-(3-Ethoxy-4-methoxyphenyl)-3-(3,6-difluorophthalimido)-N-hydroxypropionamide was prepared by the procedure of Example 1 from 3-(3-ethoxy-4-methoxyphenyl)-3-(3,6-difluorophthalimido)propanoic acid (580 mg, 1.43 mmol), carbonyldiimidazole (255 mg, 1.57 mmol) and hydroxylamine hydrochloride (120 mg, 1.73 mmol) in tetrahydrofuran (8 mL) to afford 3-(3-ethoxy-4-methoxyphenyl)-3-(3,6-difluorophthalimido)-N-hydroxypropionamide as a white solid (340 mg, 57% yield): mp, 171.0–172.0° C.; $^1$H NMR (DMSO-d$_6$) δ1.32 (t, J=6.9 Hz, 3H, CH$_3$), 3.03 (dd, J=7.9, 14.8 Hz, 1H, CHH), 3.16 (dd, J=8.1, 14.9 Hz, 1H, CHH), 3.71 (s, 3H, CH$_3$), 3.91 (q, J=6.9 Hz, 2H, CH$_2$), 5.62 (t, J=7.8 Hz, 1H, NCH), 6.878–6.95 (m, 2H, Ar), 6.99 (br s, 1H, Ar), 7.74 (t, $J_{H-F}$=5.8 Hz, 2H, Ar), 8.81 (br s, 1H, OH), 10.61 (br s, 1H, NH); $^{13}$C NMR (DMSO-d$_6$) δ14.64, 33.88, 50.29, 55.44, 63.71, 111.64, 112.44, 118.02 (t, $J_{C-F}$=9.2 Hz), 119.77, 125.47 (t, $J_{C-F}$=15 Hz), 130.42, 147.65, 148.59, 152.93 (dd, $J_{C-F}$=4.2, 261 Hz), 163.49, 165.84; Anal Calcd for C$_{20}$H$_{18}$N$_2$O$_6$F$_2$: C, 57.14; H, 4.32; N, 6.66. Found: C, 56.93; H, 4.37; N, 6.31.

EXAMPLE 16

3-(4-Aminophthalimido)-3-(3-ethoxy-4methoxyphenyl)-N-hydroxypropionamide

A mixture of N-Benzyloxy-3-(3-ethoxy-4-methoxyphenyl)-3-(4-nitrophthalimido)propionamide (2.3 g, 4.42 mmol) and Pd(OH)$_2$/C (600 mg) in ethyl acetate/methanol/tetrahydrofuran (150 mL each) was shaken under hydrogen. After 24 hours the suspension was filtered through a pad of Celite, and then was washed with methanol (30 mL) and methylene chloride (30 mL). The filtrate was concentrated in vacuo to give an oil. The oil was stirred with ethyl acetate (10 mL) to afford 3-(4-aminophthalimido)-3-(3-ethoxy-4-methoxyphenyl)-N-hydroxypropionamide as a yellow solid (1.8 g, 100% yield): mp, 193.0–195.0° C.; $^1$H NMR (DMSO-d$_6$) δ1.31 (t, J=6.9 Hz, 3H, CH$_3$), 3.05 (d, J=7.9 Hz, 2H, CH$_2$), 3.71 (s, 3H, CH$_3$), 3.96 (q, J=7.0 Hz, 2H, CH$_2$), 5.57 (t, J=7.9 Hz, 1H, NCH), 6.47 (br s, 2H, NH$_2$), 6.77 (dd, J=2.0, 8.3 Hz, 1H, Ar), 6.83–6.88 (m, 3H, Ar), 6.99 (br s, 1H, Ar), 7.45 (d, J=8.3 Hz, 1H, Ar), 8.78 (br s, 1H, OH), 10.55 (1H, NH); $^{13}$C NMR (DMSO-d$_6$) δ14.69, 34.51, 49.75, 55.45, 63.73, 106.82, 111.74, 112.38, 116.32, 116.73, 119.60, 124.89, 131.85, 134.18, 147.62, 148.42, 155.00, 166.111, 167.70, 168.00; Anal Calcd for C$_{20}$H$_{21}$N$_3$O$_6$: C, 60.14; H, 5.30; N, 10.52. Found: C, 60.00; H, 5.34; N, 10.30.

EXAMPLE 17

N-Hydroxy-3-(3,4-dimethoxyphenyl)-3-(1-oxoisoindolinyl)propionamide

N-Hydroxy-3-(3,4-dimethoxyphenyl)-3-(1-oxoisoindolinyl)propionamide was prepared by the procedure of Example 1 from 3-(3,4-dimethoxyphenyl)-3-(1-oxoisoindolinyl)propanoic acid (5.00 g, 14.7 mmol), carbonyldiimidazole (2.49 g, 15.4 mmol) and hydroxylamine hydrochloride (1.30 g, 19.1 mmol) in tetrahydrofuran (15 mL) to afford N-hydroxy-3-(3,4-dimethoxyphenyl)-3-(1-oxoisoindolinyl)propionamide as a white solid (4.1 g, 79% yield): mp, 188.5–189.5° C.; $^1$H NMR (DMSO-d$_6$) δ2.82–2.87 (m, 2H, CH$_2$), 3.71 (s, 3H, CH$_3$), 3.74 (s, 3H, CH$_3$), 4.15 (d, J=17.5 Hz, NCHH), 4.63 (d, J=17.5 Hz, 1H, NCHH), 5.74 (t, J=7.7 Hz, 1H, NCR), 6.85–6.93 (m, 3H, Ar), 7.45–7.69 (m, 4H, Ar), 8.83 (br s, 1H, OH), 10.60 (1H, NH); $^{13}$C NMR (DMSO-d$_6$) δ35.11, 46.26, 51.25, 55.50, 111.09, 111.76, 119.19, 122.79, 123.43, 127.84, 131.29, 131.91, 132.27, 141.68, 148.27, 148.69, 166.03, 166.84; Anal Calcd for C$_{19}$H$_{20}$N$_2$O$_5$: C, 64.04; H, 5.66; N, 7.86. Found: C, 64.08; H, 5.55; N, 7.86.

EXAMPLE 18

3-(3-Cyclopentyloxy-4-methoxyphenyl)-N-hydroxy-3-(1-oxoisoindolinyl)propionamide 3-(3-Cyclopentyloxy-4-methoxyphenyl)-N-hydroxy-3-(1-oxoisoindolinyl)propionamide was prepared by the procedure of Example 1 from 3-(3-cyclopentyloxy-4-methoxyphenyl)-3-(1-oxoisoindolinyl)propanoic acid (1.00 g, 2.53 mmol), carbonyldiimidazole (430 mg, 2.66 mmol) and hydroxylamine hydrochloride (230 mg, 3.29 mmol) in tetrahydrofuran (5 mL) to afford 3-(3-cyclopentyloxy-4-methoxyphenyl)-N-hydroxy-3-(1-oxoisoindolinyl) propionamide as a white solid (950 mg, 91% yield): mp, 183.0–184.5° C.; $^1$H NMR (DMSO-d$_6$) δ1.54–1.82 (m, 8H, C$_5$H$_8$), 2.82–2.86 (m, 2H, CH$_2$), 3.70 (s, 3H, CH$_3$), 4.13 (d, J=17.5 Hz, NCHH), 4.55 (d, J=17.5 Hz, 1H, NCHH), 4.73

(m, 1H, CH), 5.74 (t, J=7.6 Hz, 1H, NCH), 6.85–6.93 (m, 3H, Ar), 7.47–7.70 (m, 4H, Ar), 8.84 (br s, 1H, OH), 10.60 (1H, NH); $^{13}$C NMR (DMSO-$d_6$) $\delta$23.50, 32.11, 32.18, 46.20, 51.17, 55.53, 79.52, 112.21, 114.00, 119.14, 122.78, 123.43, 127.85, 131.31, 131.86, 132.27, 141.65, 146.87, 149.07, 166.04, 166.91; Anal Calcd for $C_{23}H_{26}N_2O_5$ 0.7$H_2O$: C, 65.30; H, 6.53; N, 6.62. Found: C, 65.59; H, 6.38; N, 6.65; $H_2O$, 2.94.

EXAMPLE 19

N-Benzyloxy-3-(3-ethoxy-4methoxyphenyl)-3-(4-nitrophthalimido)propionamide

N-Benzyloxy-3-(3-ethoxy-4-methoxyphenyl)-3-(4-nitrophthalimido)propionamide was prepared by the procedure of Example 1 from 3-(3-ethoxy-4-methoxyphenyl)-3-(4-nitrophthalimido)propanoic acid (2.84 g, 6.85 mmol), carbonyldiimidazole (1.22 g, 7.52 mmol) and O-benzylhydroxylamine hydrochloride (1.32 g, 8.27 mmol) in tetrahydrofuran (15 mL) to afford N-benzyloxy-3-(3-ethoxy-4-methoxyphenyl)-3-(4-nitrophthalimido)-propionamide as a yellow solid (2.1 g, 59% yield): mp, 159.0–161.0° C.; $^1$H NMR (DMSO-$d_6$) $\delta$1.30 (t, J=6.9 Hz, 3H, $CH_3$), 3.03 (dd, J=7.7, 14.8 Hz, 1H, CHH), 3.15 (dd, J=8.0, 14.9 Hz, 1H, CHH), 3.72 (s, 3H, $CH_3$), 3.96 (q, J=6.9 Hz, 2H, $CH_2$), 4.64 (s, 2H, PhCH$_2$), 5.66 (t, J=7.8 Hz, 1H, NCH), 6.87–6.95 (m, 2H, Ar), 6.99 (br s, 1H, Ar), 7.23–7.41 (m, 5H, Ar), 8.06 (t, J=7.7 Hz, 1H, Ar), 8.14–8.18 (m, 1H, Ar), 8.26–8.31 (m, 1H, Ar), 11.24 (br s, 1H, NH); $^{13}$C NMR (DMSO-$d_6$) $\delta$14.66, 34.09, 50.62, 55.46, 63.72, 76.69, 111.86, 112.46, 119.83, 122.47, 126.94, 128.18, 128.67, 130.28, 133.08, 135.79, 136.38, 144.36, 147.69, 148.68, 162.99, 165.69, 166.18. Anal. Calcd for $C_{27}H_{25}N_3O_8$: C, 62.42; H, 4.85; N, 8.09. Found: C, 62.12; H, 4.92; N, 7.82.

EXAMPLE 20

3-(3-Aminophthalimido)-3-(3-ethoxy-4methoxyphenyl)-N-hydroxypropionamide

A mixture of N-benzyloxy-3-(3-ethoxy-4-methoxyphenyl)-3-(3-nitrophthalimido)propionamide (1.32 g, 2.54 mmol) and 10% Pd/C (230 mg) in ethyl acetate/methanol (150 mL each) was shaken under 50–60 psi of $H_2$. After 3 days, the suspension was filtered through a pad of Celite, and the pad washed with methanol (75 mL) and methylene chloride (75 mL). The filtrate was concentrated in vacuo to give an oil. The oil was stirred with ether (20 mL) to afford 3-(3-aminophthalimido)-3-(3-ethoxy-4-methoxyphenyl)-N-hydroxypropionamide as a yellow solid (650 mg, 64% yield): mp, 143.0–145.0° C.; $^1$H NMR (DMSO-$d_6$) $\delta$1.39 (t, J=6.9 Hz, 3H, $CH_3$), 3.16 (d, J=7.8 Hz, 2H, $CH_2$), 3.79 (s, 3H, $CH_3$), 4.05 (q, J=6.9 Hz, 2H, $CH_2$), 5.68 (t, J=7.8 Hz, 1H, NCH), 6.55 (br s, 2H, $NH_2$), 6.98–7.08 (m, 5H, Ar), 7.47–7.53 (m, 1H, Ar), 8.88 (br s, 1H, OH), 10.66 (1H, NH); $^{13}$C NMR (DMSO-$d_6$) $\delta$14.70, 34.37, 49.65, 55.47, 63.75, 108.64, 110.68, 111.77, 112.39, 119.61, 121.40, 131.69, 132.03, 135.19, 146.48, 147.65, 148.47, 166.14, 167.81, 169.18; Anal Calcd for $C_{20}H_{21}N_3O_6$: C, 60.14; H, 5.30; N, 10.52. Found: C, 59.76; H, 5.21; N, 10.30.

EXAMPLE 21

N-Hydroxy-N-methyl-3-(3-ethoxy-4-methoxyphenyl)-3-(1-oxoisoindolinyl)propionamide N-Hydroxy-3-(3-ethoxy-4-methoxyphenyl)-3-(1-oxoisoindolinyl)propionamide was prepared by the procedure of Example 1 from 3-(3-ethoxy-4-methoxyphenyl)-3-(1-oxoisoindolinyl)propanoic acid (1.0 g, 2.8 mmol), carbonyldiimidazole (500 mg, 3.1 mmol) and N-methyl-hydroxylamine hydrochloride (300 mg, 3.5 mmol) in tetrahydrofuran (10 mL) to afford N-hydroxy-N-methyl-3-(3-ethoxy-4-methoxyphenyl)-3-(1-oxoisoindolinyl) propionamide as a white solid (650 mg, 61% yield): mp, 122.0–124.5° C.; $^1$H NMR (CDCl$_3$) $\delta$1.43 (t, J=7.0 Hz, 3H, $CH_3$), 3.14 (s, 3H, NCH$_3$), 3.37–3.48 (m, 2H, $CH_2$), 3.86 (s, 3H, $CH_3$), 4.02 (q, J=7.0 Hz, 2H, $CH_2$), 4.11 (d, J=17.2 Hz, NCHH), 4.51 (d, J=17.2 Hz, 1H, NCHH), 5.95 (dd, J=6.5, 10.9 Hz, 1H, NCH), 6.83–6.97 (m, 3H, Ar), 7.34–7.55 (m, 3H, Ar), 7.81 (d, J=7.1 Hz, 1H, Ar), 9.44 (br s, 1H, OH); $^{13}$C NMR (DMSO-$d_6$) $\delta$14.71, 36.04, 38.11, 48.14, 52.36, 55.95, 64.52, 111.42, 112.42, 119.45, 122.95, 123.63, 128.06, 130.57, 131.88, 141.72, 148.65, 149.18, 170.00, 170.17; Anal Calcd for $C_{21}H_{24}N_2O_5$: C, 65.61; H, 6.29; N, 7.29. Found: C, 65.56; H, 6.26; N, 7.09.

EXAMPLE 22

N-Hydroxy-3-(3-(1-methyl)ethoxy-4-methoxyphenyl)-3-(1-oxoisoindolinyl)propionamide N-Hydroxy-3-(3-(1-methyl)ethoxy-4-methoxyphenyl)-3-(1-oxoisoindolinyl)propionamide was prepared by the procedure of Example 1 from 3-(3-(1-methyl)ethoxy-4-methoxyphenyl)-3-(1-oxoisoindolinyl)propanoic acid (500 mg, 1.35 mmol), carbonyldiimidazole (230 mg, 1.42 mmol) and hydroxylamine hydrochloride (120 mg, 1.75 mmol) in tetrahydrofuran (5 mL) to afford N-hydroxy-3-(3-(1-methyl)ethoxy-4-methoxyphenyl)-3-(1-oxoisoindolinyl) propionamide as a white solid (4.1 g, 79% yield): mp, 173.0–174.0° C.; $^1$H NMR (DMSO-$d_6$) $\delta$1.19 (d, J=8.2 Hz, 3H, $CH_3$), 1.23 (d, J=8.2 Hz, 3H, $CH_3$), 2.82–2.85 (m, 2H, $CH_2$), 3.71 (s, 3H, $CH_3$), 4.11 (d, J=17.5 Hz, NCHH), 4.46–4.58 (m, 2H, CH, NCHH), 5.73 (t, J=7.5 Hz, 1H, NCH), 6.86–6.93 (m, 3H, Ar), 7.47–7.69 (m, 4H, Ar), 8.83 (br s, 1H, OH), 10.60 (1H, NH); $^{13}$C NMR (DMSO-$d_6$) $\delta$21.99, 22.09, 35.17, 46.41, 51.35, 55.67, 70.61, 112.48, 115.08, 119.79, 122.97, 123.62, 178.05, 131.51, 132.04, 132.45, 141.83, 146.71, 149.63, 166.23, 167.07; Anal Calcd for $C_{21}H_{24}N_2O_5$: C, 65.61; H, 6.29; N, 7.29. Found: C, 60.58; H, 6.18; N, 6.47.

EXAMPLE 23

3-(3-Ethoxy-4-methoxyphenyl)-N-hydroxy-3-(3-hydroxyphthalimido)propionamide 3-(3-Ethoxy-4-methoxyphenyl)-N-hydroxy-3-(3-hydroxyphthalimido)propionamide was prepared by the procedure of Example 1 from 3-(3-ethoxy-4-methoxyphenyl)-3-(3-hydroxyphthalimido)propanoic acid (0.70 g, 1.8 mmol), carbonyldiimidazole (690 mg, 4.25 mmol) and hydroxylamine hydrochloride (380 mg, 5.47 mmol) in tetrahydrofuran (10 mL) to afford 3-(3-ethoxy-4-methoxyphenyl)-N-hydroxy-3-(3-hydroxyphthalimido) propionamide as a yellow solid (580 mg, 80% yield): mp, 209.0–210.0° C.; $^1$H NMR (DMSO-$d_6$) $\delta$1.31 (t, J=6.9 Hz, 3H, $CH_3$), 3.08 (d, J=7.9 Hz, 2H, $CH_2$), 3.71 (s, 3H, $CH_3$), 3.97 (q, J=6.9 Hz, 2H, $CH_2$), 5.62 (t, J=7.9 Hz, 1H, NCH), 6.88 (br s, 2H, Ar), 6.99 (br s, 1H, Ar), 7.18 (d, J=8.3 Hz, 1H, Ar), 7.22 (d, J=7.1 Hz, 1H, Ar), 7.58 (dd, J=7.4, 8.2 Hz, 1H, Ar), 8.88 (br s, 1H, OH), 10.58 (br s, 1H, NH); $^{13}$C NMR (DMSO-$d_6$) $\delta$24.73, 44.31, 59.77, 65.49, 73.77, 121.76, 122.40, 123.84, 124.29, 129.66, 133.41, 141.53, 143.24, 146.04, 157.66, 158.49, 165.49, 176.14, 176.39, 177.51; Anal Calcd for $C_{20}H_{20}N_2O_7$: C, 60.00; H, 5.03; N, 7.00. Found: C, 59.99; H, 5.08; N, 7.03.

EXAMPLE 24

3-(3-Ethoxy-4-methoxyphenyl)-N-hydroxy-3-(4-hydroxyphthalimido)propionamide 3-(3-Ethoxy-4-methoxyphenyl)-N-hydroxy-3-(4-hydroxyphthalimido)propionamide was prepared by the procedure of Example 1 from 3-(3-ethoxy-4-methoxyphenyl)-3-(4-hydroxyphthalimido)propanoic acid (4.0 g, 10.4 mmol), carbonyldiimidazole (2.02 g, 12.46 mmol) and hydroxylamine hydrochloride (1.13 g, 16.3 mmol) in tetrahydrofuran (20 mL) to afford 3-(3-ethoxy-4-methoxyphenyl)-N-hydroxy-3-(4-hydroxyphthalimido) propionamide as a yellow solid (1.8 g, 44% yield): mp, 143.5–146.0° C.; $^1$H NMR (DMSO-$d_6$) $\delta$1.31 (t, J=6.9 Hz, 3H, $CH_3$), 3.09 (d, J=7.9 Hz, 2H, $CH_2$), 3.72 (s, 3H, $CH_3$), 3.98 (q, J=6.9 Hz, 2H, $CH_2$), 5.62 (t, J=7.9 Hz, 1H, NCH), 6.89 (br s, 2H, Ar), 7.01 (br s, 1H, Ar), 7.09–7.12 (m, 2H, Ar), 7.66–7.69 (m, 1H, Ar), 8.88 (br s, 1H, OH), 10.59 (br s, 1H, NH); $^{13}$C NMR (DMSO-$d_6$) $\delta$24.71, 44.39, 60.08, 65.47, 73.75, 119.72, 121.76, 122.36, 129.66, 130.53, 131.37, 135.32, 141.49, 144.08, 157.68, 158.51, 173.43, 176.09, 177.49; Anal Calcd for $C_{20}H_{20}N_2O_7$+0.35$H_2O$: C, 59.07; H, 5.13; N, 6.89. Found: C, 58.84; H, 5.05; N, 7.26.

EXAMPLE 25

3-(3-Ethoxy-4methoxyphenyl)-N-hydroxy-3-(3-methylphthalimido)propionamide 3-(3-Ethoxy-4-methoxyphenyl)-N-hydroxy-3-(3-methylphthalimido)propionamide was prepared by the procedure of Example 1 from 3-(3-ethoxy-4-methoxyphenyl)-3-(3-methylphthalimido)propanoic acid (1.50 g, 3.91 mmol), carbonyldiimidazole (698 mg, 4.30 mmol) and hydroxylamine hydrochloride (330 mg, 4.75 mmol) in tetrahydrofuran (5 mL) to afford 3-(3-ethoxy-4-methoxyphenyl)-N-hydroxy-3-(3-methylphthalimido) propionamide as a white solid (1.4 g, 90% yield): mp, 165.0–166.5° C.; $^1$H NMR (DMSO-$d_6$) $\delta$1.32 (t, J=6.9 Hz, 3H, $CH_3$), 2.61 (s, 3H, $CH_3$), 3.10 (d, J=7.9 Hz, 2H, $CH_2$), 3.72 (s, 3H, $CH_3$), 3.98 (q, J=7.0 Hz, 2H, $CH_2$), 5.66 (t, J=7.8 Hz, 1H, NCH), 6.87–6.90 (m, 2H, Ar), 7.02 (br s, 1H, Ar), 7.57–7.69 (m, 3H, Ar), 8.80 (br s, 1H, OH), 10.59 (br s, 1H, NH); $^{13}$C NMR (DMSO-$d_6$) $\delta$14.71, 16.99, 34.21, 49.95, 55.45, 63.73, 111.72, 112.38, 119.70, 120.76, 127.79, 131.27, 131.67, 134.06, 136.66, 137.29, 147.65, 148.51, 166.06, 167.55, 168.31; Anal Calcd for $C_{21}H_{22}N_2O_6$+$H_2O$: C, 60.57; H, 5.81; N, 6.73. Found: C, 60.83; H, 5.72; N, 6.53.

EXAMPLE 26

3-(3-Acetoamidophthalimido)-3-(3-ethoxy-4-methoxyphenyl)-N-hydroxypropionamide 3-(3-Acetoamidophthalimido)-3-(3-ethoxy-4-methoxyphenyl)-N-hydroxypropionamide was prepared by the procedure of Example 1 from 3-(3-acetoamidophthalimido)-3-(3-ethoxy-4-methoxyphenyl) propanoic acid (2.0 g, 4.7 mmol), carbonyldiimidazole (1.14 g, 7.03 mmol) and hydroxylamine hydrochloride (651 mg, 9.37 mmol) in tetrahydrofuran (10 mL) to afford 3-(3-acetoamidophthalimido)-3-(3-ethoxy-4-methoxyphenyl)-N-hydroxypropionamide as a white solid (1.0 g, 48% yield): mp, 117.0–119.0° C.; $^1$H NMR (DMSO-$d_6$) $\delta$1.31 (t, J=6.9 Hz, 3H, $CH_3$), 2.19 (s, 3H, $CH_3$), 3.09 (d, J=7.9 Hz, 2H, $CH_2$), 3.72 (s, 3H, $CH_3$), 3.98 (q, J=7.0 Hz, 2H, $CH_2$), 5.65 (t, J=7.8 Hz, 1H, NCH), 6.87–6.95 (m, 2H, Ar), 6.99 (br s, 1H, Ar), 7.54 (d, J=6.9 Hz, 1H, Ar), 7.77 (t, J=7.45 Hz, 1H, Ar), 8.41–8.47 (m, 1H, Ar), 8.80 (br s, 1H, OH), 9.71 (s, 1H, NH), 10.59 (br s, 1H, NH); $^{13}$C NMR (DMSO-$d_6$) $\delta$24.69, 34.20, 44.09, 60.04, 65.48, 73.79, 121.78, 122.43, 126.69, 127.97, 129.64, 135.83, 141.00, 141.44, 145.75, 146.38, 157.70, 158.59, 175.97, 177.13, 178.19, 179.22; Anal Calcd for $C_{22}H_{23}N_3O_7$+0.3$H_2O$: C, 59.14; H, 5.32; N, 9.40. Found: C, 59.32; H, 5.33; N, 9.02.

EXAMPLE 27

3-(4-Acetoamidophthalimido)-3-(3-ethoxy-4-methoxyphenyl)-N-hydroxypropionamide 3-(4-Acetoamidophthalimido)-3-(3-ethoxy-4-methoxyphenyl)-N-hydroxypropionamide was prepared by the procedure of Example 1 from 3-(4-acetoamidophthalimido)-3-(3-ethoxy-4-methoxyphenyl) propanoic acid (2.0 g, 4.7 mmol), carbonyldiimidazole (836 mg, 5.16 mmol) and hydroxylamine hydrochloride (391 mg, 5.63 mmol) in tetrahydrofuran (8 mL) to afford 3-(4-acetoamidophthalimido)-3-(3-ethoxy-4-methoxyphenyl)-N-hydroxypropionamide as a yellow solid (0.9 g, 43% yield): mp, 138.0–140.0° C.; $^1$H NMR (DMSO-$d_6$) $\delta$1.31 (t, J=6.9 Hz, 3H, $CH_3$), 2.12 (s, 3H, $CH_3$), 3.09 (d, J=7.9 Hz, 2H, $CH_2$), 3.72 (s, 3H, $CH_3$), 3.98 (q, J=6.9 Hz, 2H, $CH_2$), 5.64 (t, J=7.8 Hz, 1H, NCH), 6.89 (br s, 2H, Ar), 7.01 (br s, 1H, Ar), 7.77–7.86 (m, 2H, Ar), 8.17 (br s, 1H, Ar), 8.80 (br s, 1H, OH), 10.58 (br s, 2H, 2NH); $^{13}$C NMR (DMSO-$d_6$) $\delta$14.69, 24.18, 34.27, 50.15, 55.43, 63.69, 111.68, 112.26, 112.46, 119.63, 123.11, 124.37, 124.79, 131.26, 132.76, 114.87, 147.65, 148.48, 165.98, 167.26, 169.22; Anal Calcd for $C_{22}H_{23}N_3O_7$: C, 59.86; H, 5.25; N, 9.52. Found: C, 59.49; H, 5.24; N, 9.40.

EXAMPLE 28

3-(3-Ethoxy-4-methoxyphenyl)-N-hydroxy-3-(1,3-dioxo-2,3-dihydro-1H-benzo[e]isoindol-2'-yl) propionamide 3-(3-Ethoxy-4-methoxyphenyl)-N-hydroxy-3-(1,3-dioxo-2,3-dihydro-1H-benzo[e]-isoindol-2'-yl) propionamide was prepared by the procedure of Example 1 from 3-(3-ethoxy-4-methoxyphenyl)-3-(1,3-dioxo-2,3-dihydro-1H-benzo[e]isoindol-2'-yl)propanoic acid (1.50 g, 3.57 mmol), carbonyldiimidazole (609 mg, 3.76 mmol) and hydroxylamine hydrochloride (287 mg, 4.13 mmol) in tetrahydrofuran (8 mL) to afford 3-(3-ethoxy-4-methoxyphenyl)-N-hydroxy-3-(1,3-dioxo-2,3-dihydro-1H-benzo[e]isoindol-2'-yl)-propionamide as a yellow solid (1.14 g, 74% yield): mp, 160.0° C.; $^1$H NMR (DMSO-$d_6$) $\delta$1.31 (t, J=6.9 Hz, 3H, $CH_3$), 3.15 (d, J=7.8 Hz, 2H, $CH_2$), 3.72 (s, 3H, $CH_3$), 3.99 (q, J=7.0 Hz, 2H, $CH_2$), 5.72 (t, J=7.7 Hz, 1H, NCH), 6.88–7.07 (m, 3H, Ar), 7.71–7.88 (m, 3H, Ar), 8.15 (d, J=8.0 Hz, 1H, Ar), 8.37 (d, J=8.2 Hz, 1H, Ar), 8.78 (m, 2H, OH, Ar), 10.62 (br s, 1H, NH); $^{13}$C NMR (DMSO-$d_6$) $\delta$14.70, 34.40, 50.12, 55.44, 63.72, 111.72, 112.36, 118.39, 119.68, 122.79, 126.22, 127.09, 128.84, 129.16, 129.88, 130.75, 131.30, 135.48, 136.18, 147.70, 148.51, 168.09, 168.13, 168.89; Anal Calcd for $C_{24}H_{22}N_2O_6$+0.4$H_2O$: C, 65.27; H, 5.20; N, 6.34. Found: C, 65.30; H, 5.17; N, 6.46.

EXAMPLE 29

3-(4-tert-Butylphthalimido)-3-(3-ethoxy-4methoxyphenyl)-N-hydroxypropionamide 3-(4-tert-Butylphthalimido)-3-(3-ethoxy-4-methoxyphenyl)-N-hydroxypropionamide was prepared by the procedure of Example 1 from 3-(4-tert-butylphthalimido)-3-(3-ethoxy-4-methoxyphenyl)propanoic acid (2.0 g, 4.7 mmol), carbonyldiimidazole (800 mg, 4.93 mmol) and hydroxylamine hydrochloride (377 mg, 5.43 mmol) in tetrahydrofuran (10 mL) to afford 3-(4-tert-butylphthalimido)-3-(3-ethoxy-4-methoxyphenyl)-N-hydroxypropionamide as a white solid (1.77 g, 85% yield): mp, 127.5–129.5° C.; $^1$H NMR (DMSO-d$_6$) δ1.24–1.44 (m, 12H, 4CH$_3$), 3.09 (d, J=7.9 Hz, 2H, CH$_2$), 3.71 (s, 3H, CH$_3$), 3.97 (q, J=6.9 Hz, 2H, CH$_2$), 5.66 (t, J=7.8 Hz, 1H, NCH), 6.89 (br s, 2H, Ar), 7.01 (br s, 1H, Ar), 7.76–7.87 (m, 3H, Ar), 8.79 (br s, 1H, OH), 10.59 (br s, 1H, NH); $^{13}$C NMR (DMSO-d$_6$) δ14.73, 30.76, 34.29, 35.48, 50.14, 55.46, 63.72, 111.69, 112.27, 119.59, 119.98, 123.07, 128.75, 131.28, 131.45, 131.55, 147.69, 148.49, 158.32, 166.07, 167.53, 167.85; Anal Calcd for C$_{24}$H$_{28}$N$_2$O$_6$: C, 65.44; H, 6.41; N, 6.36. Found: C, 64.34; H, 6.29; N, 7.04.

EXAMPLE 30

3-(3,4-dimethoxyphenyl)-N-hydroxy-3-(1,3-dioxo-2,3-dihydro-1H-benzo[e]-isoindol-2'-yl)propionamide 3-(3,4-Dimethoxyphenyl)-N-hydroxy-3-(1,3-dioxo-2,3-dihydro-1H-benzo[e]isoindol-2'-yl)propionamide was prepared by the procedure of Example 1 from 3-(3,4-dimethoxyphenyl)-3-(1,3-dioxo-2,3-dihydro-1H-benzo[e]isoindol-2'-yl)propanoic acid (0.90 g, 2.2 mmol), carbonyldiimidazole (382 mg, 2.36 mmol) and hydroxylamine hydrochloride (180 mg, 2.59 mmol) in tetrahydrofuran (10 mL) to afford 3-(3,4-dimethoxyphenyl)-N-hydroxy-3-(1,3-dioxo-2,3-dihydro-1H-benzo[e]isoindol-2'-yl)-propionamide as a yellow solid (150 mg, 15% yield): mp, 218.0–220.0° C.; $^1$H NMR (DMSO-d$_6$) δ3.17 (d, J=7.8 Hz, 2H, CH$_2$), 3.72 (s, 3H, CH$_3$), 3.75 (s, 3H, CH$_3$), 5.74 (t, J=7.8 Hz, 1H, NCH), 6.88–7.01 (m, 2H, Ar), 7.08 (br s, 1H, Ar), 7.75–7.89 (m, 3H, Ar), 8.17 (d, J=8.0 Hz, 1H, Ar), 8.40 (d, J=8.2 Hz, 1H, Ar), 8.78–8.81 (m, 2H, OH, Ar), 10.62 (br s, 1H, NH); $^{13}$C NMR (DMSO-d$_6$) δ34.42, 50.11, 55.48, 111.29, 111.66, 118.35, 119.59, 123.77, 126.21, 127.08, 128.80, 129.13, 129.84, 130.73, 131.38, 135.44, 136.16, 148.35, 148.53, 168.06, 168.09, 168.86; Anal Calcd for C$_{23}$H$_{20}$N$_2$O$_6$: C, 65.71; H, 4.79; N, 6.66. Found: C, 65.06; H, 4.62; N, 6.44.

EXAMPLE 31

3-(3,4-Dimethoxyphthalimido)-3-(3-ethoxy-4-methoxyphenyl)-N-hydroxypropionamide 3-(3,4-Dimethoxyphthalimido)-3-(3-ethoxy-4-methoxyphenyl)-N-hydroxypropionamide was prepared by the procedure of Example 1 from 3-(3,4-Dimethoxyphthalimido)-3-(3-ethoxy-4-methoxyphenyl)-N-hydroxypropanoic acid (0.83 g, 1.9 mmol), carbonyldiimidazole (501 mg, 3.09 mmol) and hydroxylamine hydrochloride (268 mg, 3.86 mmol) in tetrahydrofuran (10 mL) to afford 3-(3,4-dimethoxyphthalimido)-3-(3-ethoxy-4-methoxyphenyl)-N-hydroxypropionamide as a white solid (130 mg, 15% yield): mp, 158.0; $^1$H NMR (DMSO-d$_6$) δ1.31 (t, J=7.0 Hz, 3H, CH$_3$), 3.08 (d, J=7.8 Hz, 2H, CH$_2$), 3.72 (s, 3H, CH$_3$), 3.92 (s, 3H, CH$_3$), 3.94 (s, 3H, CH$_3$), 3.97 (q, J=7.0 Hz, 2H, CH$_2$), 5.62 (t, J=7.9 Hz, 1H, NCH), 6.89 (br s, 2H, Ar), 7.00 (br s, 1H, Ar), 7.35–7.38 (m, 1H, Ar), 7.54 (d, J=8.0 Hz, 1H, Ar), 8.78 (br s, 1H, OH), 10.56 (br s, 1H, NH); $^{13}$C NMR (DMSO-d$_6$) δ14.65, 34.25, 50.03, 55.44, 56.61, 61.73, 63.71, 105.66, 111.74, 112.41, 117.11, 119.52, 119.68, 121.53, 123.48, 131.33, 147.61, 148.49, 157.65, 165.39, 166.00, 166.82; Anal Calcd for C$_{22}$H$_{24}$N$_2$O$_8$: C, 59.45; H, 5.44; N, 6.30. Found: C, 58.01; H, 5.32; N, 6.02.

EXAMPLE 32

Tablets, each containing 50 mg of N-hydroxy-3-(3,4-dimethoxyphenyl)-3-(1-oxoisoindolinyl)propionamide, are prepared in the following manner:

| Constituents (for 1000 tablets) | |
|---|---|
| N-hydroxy-3-(3,4-dimethoxyphenyl)-3-(1-oxoisoindolinyl)-propionamide | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 33

Tablets, each containing 100 mg of N-hydroxy-3-(3,4-dimethoxyphenyl)-3-phthalimidopropionamide, can be prepared in the following manner:

| Constituents (for 1000 tablets) | |
|---|---|
| N-hydroxy-3-(3,4-dimethoxy-phenyl)-3-phthalimido-propionamide | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 34

Tablets for chewing, each containing 75 mg of 3-(3-ethoxy-4-methoxyphenyl)-N-hydroxy-3-phthalimidopropionamide, can be prepared in the following manner:

| Composition (for 1000 tablets) | |
|---|---|
| 3-(3-ethoxy-4-methoxyphenyl)-N-hydroxy-3-phthalimido-propionamide | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 3-(3-Ethoxy-4-methoxyphenyl)-N-hydroxy-3-phthalimidopropionamide, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 35

Tablets, each containing 10 mg N-benzyloxy-3-(3-ethoxy-4-methoxyphenyl)-3-(1-oxoisoindolinyl) propionamide, can be prepared in the following manner:

| Composition (for 1000 tablets) | |
|---|---|
| N-benzyloxy-3-(3-ethoxy-4-methoxyphenyl)-3-(1-oxoiso-indolinyl)propionamide | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 36

Gelatin dry-filled capsules, each containing 100 mg of N-benzyloxy-3-(3-ethoxy-4-methoxyphenyl)-3-phthalimidopropionamide, can be prepared in the following manner:

| Composition (for 1000 capsules) | |
|---|---|
| N-benzyloxy-3-(3-cyclopentylidene-methyl-4-methoxyphenyl)-3-phthalimido-propionamide | 100.0 g |
| microcrystalline cellulose | 30.0 g |
| sodium lauryl sulfate | 2.0 g |
| magnesium stearate | 8.0 g |

The sodium lauryl sulfate is sieved into the N-benzyloxy-3-(3-cyclopentylidenemethyl-4)-4-phthalimidopropionamide through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 37

A 0.2% injection or infusion solution can be prepared, for example, in the following manner:

| | |
|---|---|
| 3-(3-cyclopentyloxy-4-methoxyphenyl)-N-hydroxy-3-phthalimidopropionamide | 5.0 g |
| sodium chloride | 22.5 g |
| phosphate buffer pH 7.4 | 300.0 g |
| demineralized water | to 2500.0 mL |

3-(3-Cyclopentyloxy-4-methoxyphenyl)-N-hydroxy-3-phthalimidopropionamide is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

EXAMPLE 38

3-(3-Ethoxy-4-methoxyphenyl)-N-hydroxy-3-(3-dimethylaminophthalimido)propionamide 3-(3-Ethoxy-4-methoxyphenyl)-N-hydroxy-3-(3-dimethylaminophthalimido)-propionamide was prepared by the procedure of Example 1 from 3-(3-ethoxy-4-methoxyphenyl)-3-(3-dimethylaminophthalimido) propanoic acid (0.31 g, 0.75 mmol), carbonyldiimidazole (140 mg, 0.86 mmol) and hydroxylamine hydrochloride (66 mg, 0.95 mmol) in tetrahydrofuran (5 mL) to afford 3-(3-ethoxy-4-methoxyphenyl)-N-hydroxy-3-(3-dimethylaminophthalimido)propionamide as a yellow solid (280 mg, 87% yield): mp, 187.0–188.6° C.; $^1$H NMR (DMSO-$d_6$) δ1.31 (t, J=7.0 Hz, 3H, $CH_3$), 3.01 (s, 6H, $CH_3$), 3.08 (d, J=7.9 Hz, 2H, $CH_2$), 3.71 (s, 3H, $CH_3$), 3.97 (q, J=6.9 Hz, 2H, $CH_2$), 5.63 (t, J=7.9 Hz, 1H, NCH), 6.88 (br s, 2H, Ar), 7.00 (br s, 1H, Ar), 7.19 (m, 2H, Ar), 7.57 (dd, J=7.1, 8.3 Hz, 1H, Ar), 8.78 (br s, 1H, OH), 10.57 (br s, 1H, NH); $^{13}$C NMR (DMSO-$d_6$) δ14.66, 34.42, 42.96, 49.88, 55.45, 63.72, 111.75, 112.41, 112.71, 113.74, 119.63, 122.32, 131.61, 133.94, 134.92, 147.60, 148.43, 149.75, 166.11, 166.76, 167.56; Anal Calcd for $C_{22}H_{25}N_3O_6$: C, 61.82; H, 5.89; N, 9.83. Found: C, 61.79; H, 5.90; N, 9.58.

EXAMPLE 39

3-(6,8-Dioxo(2H-1,3-dioxolano[4,5-e]isoindolin-7-yl))-3-(3-ethoxy-4-methoxyphenyl)-N-hydroxypropionamide 3-(6,8-Dioxo(2H-1,3-dioxolano[4,5-e]isoindolin-7-yl))-3-(3-ethoxy-4-methoxy-phenyl)-N-hydroxypropionamide was prepared by the procedure of Example 13-(6,8-dioxo(2H-1,3-dioxolano[4,5-e]isoindolin-7-yl))-3-(3-ethoxy-4-methoxyphenyl)propanoic acid (1.20 g, 2.90 mmol), carbonyldiimidazole (517 mg, 3.19 mmol) and hydroxylamine hydrochloride (255 mg, 3.66 mmol) in tetrahydrofuran (8 mL) to afford 3-(6,8-Dioxo(2H-1,3-dioxolano[4,5-e]isoindolin-7-yl))-3-(3-ethoxy-4-methoxyphenyl)-N-hydroxypropionamide as an off-white solid (960 mg, 77% yield): mp, 203.0° C. (decomposed); $^1$H NMR (DMSO-$d_6$) δ1.31 (t, J=6.6 Hz, 3H, $CH_3$), 3.08 (d, J=7.5 Hz, 2H, $CH_2$), 3.72 (s, 3H, $CH_3$), 3.97 (q, J=6.9 Hz, 2H $CH_2$), 5.62 (t, J=7.3 Hz, 1H, NCH), 6.33 (s, 2H, $CH_2$), 6.89 (br s, 2H, Ar), 6.99 (br s, 1H, Ar), 7.22 (d, J=7.7 Hz, 1H, Ar), 7.37 (d, J=7.6 Hz, 1H, Ar), 8.80 (br s, 1H, Oh), 10.58 (br s, 1H, NH); $^{13}$C NMR (DMSO-$d_6$) δ14.67, 34.18, 50.12, 55.46, 63.75, 104.31, 110.73, 111.76, 111.96, 112.37, 118.56, 119.62, 124.15, 131.25, 143.56, 147.66, 148.53, 154.12, 164.74, 165.99, 166.59; Anal Calcd for $C_{21}H_{20}N_2O_8$+1$H_2O$ C, 56.50; H, 4.97; N, 6.28. Found: C, 56.22; H, 4.63; N, 6.28.

EXAMPLE 40

3-(3-Ethoxy-4-methoxyphenyl)-N-hydroxy-3-(3,4-dimethylphthalimido)propionamide 3-(3-Ethoxy-4-methoxyphenyl)-N-hydroxy-3-(3,4-dimethylphthalimido)propionamide was prepared by the procedure of Example 16 N-benzyloxy-3-(3-ethoxy-4-methoxyphenyl)-3-(3,4-dimethylphthalimido)propionamide (0.63 g, 1.25 mmol), Pd(OH)$_2$/C (100 mg) and hydrogen (50 psi) in ethyl acetate and methanol (30 mL each) to afford 3-(3-ethoxy-4-methoxyphenyl)-N-hydroxy-3-(3,4-dimethylphthalimido)propionamide as a white solid (430 mg, 84% yield): mp, 197.0–202.5° C.; $^1$H NMR (DMSO-$d_6$) δ1.31 (t, J=7.2 Hz, 3H, $CH_3$), 2.35 (s, 3H, $CH_3$), 2.56 (s, 3H, $CH_3$), 3.09 (d, J=7.9 Hz, 2H, $CH_2$), 3.71 (s, 3H, $CH_3$), 3.97 (q, J=6.9 Hz, 2H, $CH_2$), 5.65 (t, J=7.9 Hz, 1H, NCR), 6.89 (br s, 2H, Ar), 7.00 (br s, 1H, Ar), 7.59 br s, 2H, Ar), 8.78 br s, 1H, OH), 10.56 (br s, 1H, NH); $^{13}$C NMR (DMSO-$d_6$) δ13.22, 14.65, 19.33, 34.21, 49.88, 55.43, 63.72, 111.75, 112.40, 119.62, 120.39, 127.76, 129.33, 131.36, 134.71, 136.50, 145.13, 147.62, 148.48, 166.02, 167.32, 168.65; Anal Calcd for $C_{22}H_{24}N_2O_6$+0.3$H_2O$: C, 63.24; H, 5.93; N, 6.70. Found: C, 63.11; H, 5.88; N, 6.67.

What is claimed is:

1. A method of inhibiting a phosphodiesterase in a mammal which comprises administering an effective amount of a hydroxamic acid derivative selected from the group consisting of a compound of the formula:

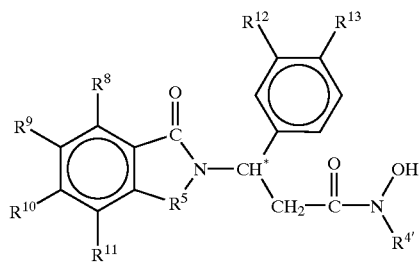

wherein
$R^{4'}$ is hydrogen or alkyl of 1 to 4 carbon atoms;
$R^5$ is C=O or $CH_2$;
each of $R^{12}$ and $R^{13}$, independently of the other, is alkoxy of 1 to 4 carbon atoms, cylcoalkoxy of 3 to 6 carbon atoms; $C_4$–$C_6$-cycloalkylidenemethyl, $C_2$–$C_{10}$-alkylidenemethyl, $C_6$–$C_{10}$-bicycloalkoxy, or indanyloxy; and
each of $R^8$, $R^9$, $R^{10}$, and $R^{11}$, independently of the others, is hydrogen, nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkyl of 1 to 10 carbon atoms, alkoxy of 1 to 10 carbon atoms, or halo.

2. The method according to claim 1 wherein in said compound $R^4$ is hydrogen.

3. The method according to claim 1 wherein in said compound each of $R^8$, $R^9$, $R^{10}$, and $R^{11}$ is hydrogen, halo, alkyl of 1 to 4 carbon atoms, or alkoxy of 1 to 4 carbon atoms.

4. A method according to claim 1 wherein in said compound one of $R^8$, $R^9$, $R^{10}$, and $R^{11}$ is amino, hydroxy, or alkyl and the others of $R^8$, $R^9$, $R^{10}$, and $R^{11}$ are hydrogen.

5. A method of inhibiting a phosphodiesterase in a mammal which comprises administering thereto an effective amount of a hydroxamic acid derivative selected from the group consisting of (a) a compound of the formula:

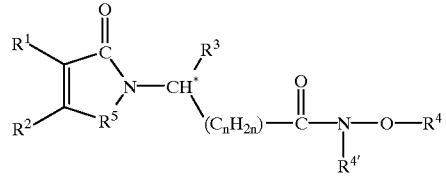

wherein
the carbon atom designated * constitutes a center of chirality;
each of $R^1$ and $R^2$, taken independently of each other is hydrogen or lower alkyl, or $R^1$ and $R^2$ taken together, together with the carbon atoms to which each is bound, is o-phenylene, o-naphthylene, or cyclohexene-1,2-diyl, unsubstituted or substituted with 1 to 4 substituents each selected independently from the group consisting of nitro, cyano, trifluoromethyl, carbethoxy, carbopropoxy, acetyl, carbamoyl, acetoxy, carboxy, hydroxy, amino, alkylamino, diakylamino, acylamino, alkyl of 1 to 10 carbon atoms, alkoxy of 1 to 10 carbon atoms, and halo;

R³ is phenyl substituted with from one to four substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, alkylthio of 1 to 10 carbon atoms, benzyloxy, cycloalkoxy of 3 to 6 carbon atoms, $C_4$–$C_6$-cycloalkylidenemethyl, $C_3$–$C_{10}$-alkylidenemethyl, indanyloxy, and halo;

R⁴ is hydrogen, alkyl of 1 to 6 carbon atoms, phenyl, or benzyl;

R⁴' is hydrogen or alkyl of 1 to 6 carbon atoms;

R⁵ is —CH₂—, —CH₂—CO—, —CO—, —SO₂—, —S—, or —NHCO—; and n has a value of 0, 1, or 2; and (b) the acid addition salts of said compound which contain a nitrogen atom capable of being protonated.

6. The method according to claim 5 wherein R¹ and R², taken together, together with the carbon atoms to which each is bound is o-phenylene or o-naphthylene, unsubsituted or substituted with 1 to 4 substituents each independently selected from the group consisting of nitro, acetyl, cyano, trifluiromethyl, carbethoxy, carbomethoxy, carbopropoxy, acetyl, carbamoyl, acetoxy, carboxy, hydroxy, amino, alkylamino, acylamino, alkyl of 1 to 10 carbon atoms, alkoxy of 1 to 10 carbon atoms, cycloalkoxy of 3 to 6 carbon atoms, and halo.

7. The method according to claim 6 wherein R¹ and R², taken together, together with the carbon atoms to which each is bound is unsubstituted o-phenylene or amino-o-phenylene.

8. The method according to claim 6 wherein R¹ and R², taken together with the carbon atoms to which each is bound is unsubstituted o-naphthylene or amino-o-naphthylene.

9. The method according to claim 6 wherein

R¹ and R², taken together with the carbon atoms to which each is bound is o-phenylene or o-naphthylene, unsubstituted or substituted with 1 to 4 carbon substituents each independently selected from the group consisting of amino, alkylamino, diakylamino, acylamino, alkyl of 1 to 4 carbon atoms, alkoxy of 1 to 4 carbon atoms, and halo; and each of R⁴ and R⁴' is hydrogen;

R⁵ is —CO— or —CH₂—; and

R³ is phenyl substituted in either or both of the 3 and 4-positions by the same or different monovalent substituent selected from the group consisting of alkoxy of 1 to 4 carbon atoms and cycloalkyloxy of 3 to 6 carbon atoms.

10. The method according to claim 5 wherein the phosphodiesterase is phosphodiesterase IV.

11. The method according to claim 5 wherein said compound is selected from the group consisting of 3-(3-ethoxy-4-methoxyphenyl)-N-hydroxy-3-(1-oxoisoindolinyl) propionamide, 3-(3-ethoxy-4-methoxyphenyl)-N-methoxy-3-(1-oxoisoindolinyl)propionamide, N-benzyloxy-3-(3-ethoxy-4-methoxyphenyl)-3-phthalimidopropionamide, N-benzyloxy-3-(3-ethoxy-4-methoxyphenyl)-3-(3-nitrophthalimido)propionamide, N-benzyloxy-3-(3-ethoxy-4-methoxyphenyl)-3-(1-oxoisoindolinyl)propionamide, 3-(3-ethoxy-4-methoxyphenyl)-N-hydroxy-3-phthalimidopropionamide, N-hydroxy-3-(3,4-dimethoxyphenyl)-3-phthalimidopropionamide, 3-(3-ethoxy-4-methoxyphenyl)-N-hydroxy-3-(3-nitrophthalimido)propionamide, N-hydroxy-3-(3,4-dimethoxyphenyl)-3-(1-oxoisoindolinyl)propionamide, 3-(3-ethoxy-4-methoxyphenyl)-N-hydroxy-3-(4-methylphthalimido)propionamide, 3-(3-cyclopentyloxy-4-methoxyphenyl)-N-hydroxy-3-phthalimidopropionamide, 3-(3-ethoxy-4-methoxyphenyl)-N-hydroxy-3-(1,3-dioxo-2,3-dihydro-1H-benzo[f]isoindol-2-yl)propionamide, N-hydroxy-3-{3-(2-propoxy)-4-methoxyphenyl}-3-phthalimidopropionamide, 3-(3-ethoxy-4-methoxy-phenyl)-3-(3,6-difluorophthalimido)-N-hydroxypropionamide, 3-(4-aminophthalimido)-3-(3-ethoxy-4-methoxyphenyl)-N-hydroxypropionamide, 3-(3-aminophthalimido)-3-(3-methoxy-4-methoxyphenyl)-N-hydroxypropionamide, 3-(3-aminophthalimido)-3-(3-ethoxy-4-methoxyphenyl)-N-hydroxypropionamide, 3-(3-aminophthalimido)-3-(3-cyclopentoxy-4-methoxyphenyl)-N-hydroxypropionamide, N-hydroxy-3-(3,4-dimethoxyphenyl)-3-(1-oxoisoindolinyl) propionamide, N-benzyloxy-3-(3-ethoxy-4-methoxyphenyl)-3-(3-nitrophthalimido)propionamide; 3-(3-cyclopentyloxy-4-methoxyphenyl)-N-hydroxy-3-(1-oxoisoindolinyl)propionamide, 3-(3-methylphthalimido)-3-(3-cyclopentoxy-4-methoxyphenyl)-N-hydroxypropionamide, 3-(4-methylphthalimido)-3-(3-cyclopentoxy-4-methoxyphenyl)-N-hydroxypropionamide, 3-(3-hydroxyphthalimido)-3-(3-cyclopentoxy-4-methoxyphenyl)-N-hydroxypropionamide, 3-(4-hydroxyphthalimido)-3-(3-cyclopentoxy-4-methoxyphenyl)-N-hydroxypropionamide, 3-(3-methylphthalimido)-3-(3-ethoxy-4-methoxyphenyl)-N-hydroxypropionamide, 3-(4-methylphthalimido)-3-(3-ethoxy-4-methoxyphenyl)-N-hydroxypropionamide, 3-(3-hydroxyphthalimido)-3-(3-ethoxy-4-methoxyphenyl)-N-hydroxypropionamide, 3-(4-hydroxyphthalimido)-3-(3-ethoxy-4-methoxyphenyl)-N-hydroxypropionamide, N-hydroxy-N-methyl-3-(3-ethoxy-4-methoxyphenyl)-3-(1-oxoisoindolinyl)propionamide, 3-(3-cyclo-pentyloxy-4-methoxyphenyl)-N-hydroxy-3-(4-ethylphthalimido) propionamide, 3-(3-ethoxy-4-methoxyphenyl)-N-hydroxy-3-(3-hydroxyphthalimido)propionamide, 3-(3-ethoxy-4-methoxyphenyl)-N-hydroxy-3-(4-hydroxyphthalimido) propionamide, 3-(3-ethoxy-4-methoxyphenyl)-N-hydroxy-3-(3-methylphthalimido)propionamide, 3-(3-acetamidophthalimido)-3-(3-ethoxy-4-methoxyphenyl)-N-hydroxypropionamide, 3-(4-acetamido-phthalimido)-3-(3-ethoxy-4-methoxyphenyl)-N-hydroxypropionamide, 3-(3-ethoxy-4-methoxyphenyl)-N-hydroxy-3-(1,3-dioxo-2,3-dihydro-1H-benzo[e]isoindol-2'-yl)prop-ionamide, 3-(4-tert-butylphthalimido)-3-(3-ethoxy-4-methoxyphenyl)-N-hydroxyprop-ionamide, 3-(3,4-dimethoxyphenyl)-N-hydroxy-3-(1,3-dioxo-2,3-dihydro-1H-benzo[e]-isoindol-2'-yl)propionamide, 3-(3,4-dimethoxyphthalimido)-3-(3-ethoxy-4-methoxy-phenyl)-N-hydroxypropionamide, 3-(3-ethoxy-4-methoxyphenyl)-N-hydroxy-3-(3-dimethylaminophthalimido)-propionamide, 3-(6,8-dioxo(2H-1,3-dioxolano[4,5-e]iso-indolin-7-yl))-3-(3-ethoxy-4-methoxyphenyl)-N-hydroxypropionamide, and 3-(3-ethoxy-4-methoxyphenyl)-N-hydroxy-3-(3,4-dimethylphthalimido) propionamide.

* * * * *